United States Patent [19]

Chasalow

[11] Patent Number: 5,643,716
[45] Date of Patent: *Jul. 1, 1997

[54] DIAGNOSTIC AGENT AND METHODS FOR IDENTIFYING HIV INFECTED INDIVIDUALS AND MONITORING THEIR THERAPY

[75] Inventor: Fred I. Chasalow, Glen Cove, N.Y.

[73] Assignee: Amur Research Corp., Glen Cove, N.Y.

[*] Notice: The term of this patent shall not extend beyond the expiration date of Pat. No. 5,464,740.

[21] Appl. No.: 465,004

[22] Filed: Jun. 5, 1995

Related U.S. Application Data

[63] Continuation of Ser. No. 65,062, May 20, 1993, Pat. No. 5,464,740, which is a continuation-in-part of Ser. No. 940,927, Sep. 8, 1992, abandoned.

[51] Int. Cl.⁶ .................................................. C12Q 1/70
[52] U.S. Cl. ........................ 435/5; 435/7.1; 435/974; 436/71
[58] Field of Search .................... 435/5, 7.1, 974; 436/71

[56] References Cited

U.S. PATENT DOCUMENTS

| | | | |
|---|---|---|---|
| 4,725,669 | 2/1988 | Essex et al. | 530/322 |
| 5,028,438 | 7/1991 | Chasalow et al. | 424/537 |
| 5,122,371 | 6/1992 | Chasalow et al. | 424/537 |
| 5,130,256 | 7/1992 | Chasalow et al. | 436/64 |

OTHER PUBLICATIONS

Gallo et al., *Science*, 224:500–502, 1984.
DeRossi et al., *Lancet*, 2:278, 1988.
Blanche et al., *New Eng. J. Med.*, 320:1643–1648, 1989.
Borkowsky et al., *Lancet*, 1:1169–1171, 1987.
Ward et al., *New Eng. J. Med.*, 318:473–478, 1988.
Moss et al., *AIDS*, 3:55–61, 1989.
Fuchs et al., *Immunology Today*, 9:150–155, 1988.
Graham et al., *New Eng. J. Med.*, 326:1037–1042, 1990.
Rakusan et al., *J. of AIDS*, 4:116–121, 1991.
Renom et al., *Res. Virol.*, 141:557–562, 1990.
Ades et al., *The Lancet*, 337:253–260, 1991.
MacDonald et al., *J. of AIDS*, 4:100–108, 1991.
Nkrumah et al., *Cen. Afr. J. of Med.*, 36:116–120, 1990.
Mortimer, *The Lancet*, 337:286–287, 1991.
Caldwell et al., *Ped. Clin. of N. Am.*, 38:1–35, 1991.
Miles, L.E.M. et al., *Lancet*, 2:492, 1968.
Berry, N.J. et al., *J. Virol. Met.*, 34:91–100, 1991.
Engvall, E. et al., *G. Immunochemistry*, 8:871, 1971. pp. 871–874.
Lieberman, S. et al., *Recent Progress in Hormone Research*, 15:165–200, 1959.
Blethen, S.L. et al., *J. Ped. Endocrin.*, 3:217–223, 1989.
Antonov P.A. Panmcheva R.P., Ivanov I.G., *Biochem. Biophys. Acta*, 835:408–410, 1985.
Benenson A. Mersel M. Pinson A., and Heller, M., *Anal. Biochem.*, 101:507–512, 1980.

*Primary Examiner*—Christine M. Nucker
*Assistant Examiner*—Jeffrey Stucker
*Attorney, Agent, or Firm*—Darby & Darby

[57] ABSTRACT

Disclosed herein are methods and a diagnostic agent for identifying HIV-infected individuals. The diagnostic agent, termed C-8.2, whose concentration is altered within about 1–3 days of HIV infection is used in assays not dependent on HIV antigens or antibodies. C-8.2 is present in the serum of all mammals and is a phospholipid or a mixture of related phospholipids.

17 Claims, 13 Drawing Sheets

DIAGNOSTIC AGENT AND METHODS FOR IDENTIFYING HIV INFECTED INDIVIDUALS AND MONITORING THEIR THERAPY

FIELD OF THE INVENTION

This application is a continuation of U.S. patent application Ser. No. 08/065,062 filed May 20, 1993, now U.S. Pat. No. 5,464,740, which is a continuation-in-part of U.S. patent application Ser. No. 07/940,927 filed Sep. 8, 1992 (now abandoned).

This invention pertains to a novel method and diagnostic agent for identifying HIV-infected individuals. The method can also be used as a surrogate end point to monitor the efficacy of anti-HIV therapeutic agents.

BACKGROUND OF THE INVENTION

Human Immunodeficiency Virus (HIV, also known as HTLV III and Lymphadenopathy virus or LAV) continues to be spread in epidemic proportions throughout the world. HIV is believed to be the causative agent of Acquired Immunodeficiency Syndrome (AIDS) and AIDS-Related Complex (ARC), a prodrome of AIDS. Although the AIDS epidemic may have leveled off in the United States and the Western World, it continues to increase in third world countries, especially Africa.

At the present time, the identification of individuals infected by HIV is based on the detection of antibodies and antigens specific for HIV in body fluids. Antibodies normally do not develop for at least a week after exposure to the virus and may not develop for up to 6 months or, in rare cases, two years. Thus, there is a long period of time during which it is not possible to determine if infection by HIV has or has not occurred. Furthermore, there are many circumstances when the detection of HIV-specific antibodies cannot be used to evaluate whether an individual is infected by HIV.

Present screening tests for identifying HIV-infected individuals are based on the detection of HIV-specific antibodies using various ligand-based techniques, such as an enzyme linked immunosorbent assay (ELISA) as originally developed by Gallo and co-workers in 1984 (Gallo, R. C. et al., *Science* 224: 500–502, 1984). Because the diagnosis of HIV infection is so devastating, after an initial positive screening test, HIV infection is confirmed by Western Blot analysis for HIV-specific antibodies. A new method for this confirmation is the demonstration of the presence of the viral genome by Polymerase Chain Reaction (PCR) analysis (DeRossi, A. et al., *Lancet* 2: 278, 1988). This confirmatory, follow-up test is 10 times more expensive than either original test. In addition, PCR analysis requires more expertise in its performance, more sophisticated materials and is subject to artifacts if not carefully controlled. Therefore, PCR will probably seldom, if ever, be used as an initial screening test for HIV infection.

Furthermore, there are circumstances when the detection of HIV-specific antibodies is not informative and there is no prior scientific basis for a screening test presently available. Non-limiting examples of circumstances where this situation prevails or may prevail are set forth below.

For example, babies of HIV-infected mothers may have maternal-derived HIV-specific antibodies but only 30% to 50% are truly HIV-infected and progress to develop AIDS (Blanche, S. et al., *N. Eng. J. Med.* 320:1643–1648, 1989). As with adults, PCR and/or tests for HIV-specific antibodies are used in an attempt to discriminate children with maternal-derived antibodies from infected babies. A positive result by either technique is perceived to be definitive of infection, but a negative result is not definitive (Borkowsky, W. et al., *Lancet* 1: 1169–1171, 1987). Repeat testing is usually necessary until: (a) maternal antibodies disappear; (b) clinical symptoms develop; (c) T-cell marker abnormalities are documented; or (d) the newborn reaches 2 years of age. Furthermore, both of these techniques are relatively expensive and, for reasons unknown at the present time, PCR does not always identify the presence of the HIV viral genome in the first few weeks of life. In summary, at the present time there is a gap in our ability to determine which infants born to HIV-infected mothers are truly HIV-infected and which only have maternal-derived HIV-specific antibodies.

There are at least 6 situations when the determination of HIV-specific antibodies is not informative. In each of these circumstances, a new diagnostic method is needed.

1. As illustrated above, to screen newborn infants of HIV-infected mothers.

2. Immediately after the occurrence of high risk events, such as an accidental needle puncture from an HIV-contaminated sample, prior to the development of HIV-specific antibodies.

3. As an adjunct for the screening of whole blood for transfusion or manufacture of blood products. Although all donated blood is currently screened before it is transfused, the screening procedures used are for HIV-specific antibodies employing ELISA and Western Blot analyses. If the donor has not yet developed antibodies (i.e. seroconverted) and is HIV-infected, the disease can be transmitted (Ward, J. W. et at., *New England Journal of Medicine* 318: 473–478, 1988). In addition, recently recipients of organ donation have been found to be HIV infected. This occurred because the organ donor was HIV-infected and had not yet developed HIV-specific antibodies and was not known to be a member of one of the high risk groups (male homosexuals, intravenous drug users and hemophiliacs) for HIV infection.

4. To identify HIV-infected patients after immunization. If an HIV vaccine is approved and used, it will not be possible to distinguish those individuals who have been vaccinated from those who are truly HIV-infected. Alternate methods of screening the blood supply will also be needed.

5. To identify new therapeutic agents and to monitor their efficacy in therapy as a surrogate end point. Currently, all such monitoring must be done by analyzing a patient's immune functions (see below).

6. As part of research studies to identify HIV-infected individuals of other species. For example, vaccine testing is now starting in animal models. After vaccination, the animals are exposed to HIV and the infection is monitored over time. However, because all infected animals have antibodies induced by the vaccine and may develop other antibodies from HIV exposure, HIV-specific antibody-based techniques cannot be used to monitor the efficacy of the vaccine. Similarly, new therapeutic agents will be tested in animal models and, again, efficacy cannot be determined by simple ELISA, or enzyme immunoassay (EIA) or other tests for HIV-specific antibodies and antigens because all of the animals will be infected and have such antibodies and antigens.

Progression to AIDS in individuals with HIV infection is presently evaluated by monitoring lymphocyte T-cell markers. Lymphocytes with T-4 antigens (also known as CD4) are present in normal (uninfected) individuals in higher concentrations than corresponding cells with T-8 antigens (also known as CD8). At the time of infection, and for part of the asymptomatic period, T-cell markers are usually within normal limits. Only as HIV infection progresses to AIDS does this ratio reverse; when the number of T-4 cells fall below 400 per ml, most patients have clinical features of AIDS. A second gap exists in the knowledge of events and markers for progression to AIDS during the asymptomatic stage of HIV infection. Currently, high levels of β-2 microglobulin have been associated with poor prognoses (Mossi, A. R. et al., *AIDS* 3: 55–61, 1989) whereas elevated levels of urinary and serum neopterin (a folic acid metabolite) have been found in individuals with HIV infection and the levels increase as AIDS develops (Fuchs, D. et al., *Immunology Today* 9: 150–155, 1988). Thus, although the complete causal relationship has not been fully elucidated, measurement of either component has been proposed to serve as a prognostic marker for AIDS, but neither can be used for the early detection of HIV infection because the above-mentioned changes in concentration occur only a significant time after infection.

What is needed in the art are new methods for determining whether a patient is infected by HIV in the situations mentioned above in which the analysis of HIV-specific antibodies is not informative.

Therefore, it is an object of the present invention to devise methods for identifying individuals who are HIV-infected.

It is a further object of the present invention to devise methods to identify HIV-infected individuals in situations where the detection of HIV-specific antibodies is not informative or practical.

A still further object of the present invention is to provide a diagnostic agent which can be employed as a surrogate end point for monitoring the therapy of HIV-infected individuals.

SUMMARY OF THE INVENTION

The present invention fulfills the above objects in the discovery of a novel factor, present in the serum of mammals, whose concentration is initially altered about 1–3 days after infection by HIV. This is a most important finding in that there are FDA-approved treatments for HIV-infected individuals, such as azidothymidine (AZT or Zidovudine) or dideoxyinosine (DDI) which may improve an HIV-infected patient's immunological functions and substantially delay the onset of AIDS-related illness in such individuals. Therefore, the earlier that a positive diagnosis of HIV infection can be determined, the sooner such therapy can be instituted (Graham, N. M. H. et al., *New England Journal of Medicine* 326: 1037–1042, 1990).

In one aspect the present invention provides a method for identifying a patient infected with HIV comprising the steps of quantifying the amount of C-8.2 in a blood or a blood fraction sample from said patient; wherein said patient is HIV infected if the amount of C-8.2 in said patient's blood or blood fraction sample is statistically different from the amount of C-8.2 in blood or blood fraction samples obtained from a control, non-HIV infected group.

In another aspect the present invention provides an isolated phospholipid having a retention time on an amino carbohydrate HPLC column of about 8.2 minutes using an acetonitrile gradient and absorbance of 210 nm of light.

A further aspect of the present invention provides a method for identifying a patient infected with HIV comprising the steps of providing a blood or blood fraction sample from said patient; quantifying the amount of C-8.2 in said sample; and comparing the amount of C-8.2 in said sample with the amount of C-8.2 present in a blood or blood fraction sample obtained from an age-matched control group of non-HIV infected individuals; wherein said patient is HIV infected if the amount of C-8.2 in said patient's sample is statistically different from the amount of C-8.2 in said control group.

A still further aspect of the present invention is directed to a method for determining the efficacy of the treatment of a human patient infected with HIV comprising the steps of providing a blood or blood fraction sample from said patient before said treatment; quantifying the amount of C-8.2 in said sample of step a.; obtaining a blood or blood fraction sample from said patient during said treatment; or obtaining a blood or blood fraction sample from said patient after said treatment, and quantifying the amount of C-8.2 in said sample of step c.; comparing the amount of C-8.2 in said sample of step a. with the amount of C-8.2 in said sample of step c; wherein said treatment is effective if the amount of C-8.2 in said sample of step a. is statistically different from the amount of C-8.2 in said sample of step c.).

In yet another aspect the present invention provides a method for identifying a patient infected with HIV comprising the steps of providing a serum sample obtained from said patient; quantifying the amount of C-8.2 in said serum sample; comparing the amount of C-8.2 in said serum sample with that of the amount of C-8.2 present in a serum sample obtained from age-matched control, non-HIV-infected group; wherein said patient is HIV infected if the amount of C-8.2 in said patient's serum sample is statistically different from the amount of C-8.2 in said control, non-HIV infected group.

These and other aspects of the present invention will be apparent to those of ordinary skill in the art in light of the present description, claims and drawings.

DETAILED DESCRIPTION OF THE INVENTION

Figure 1:
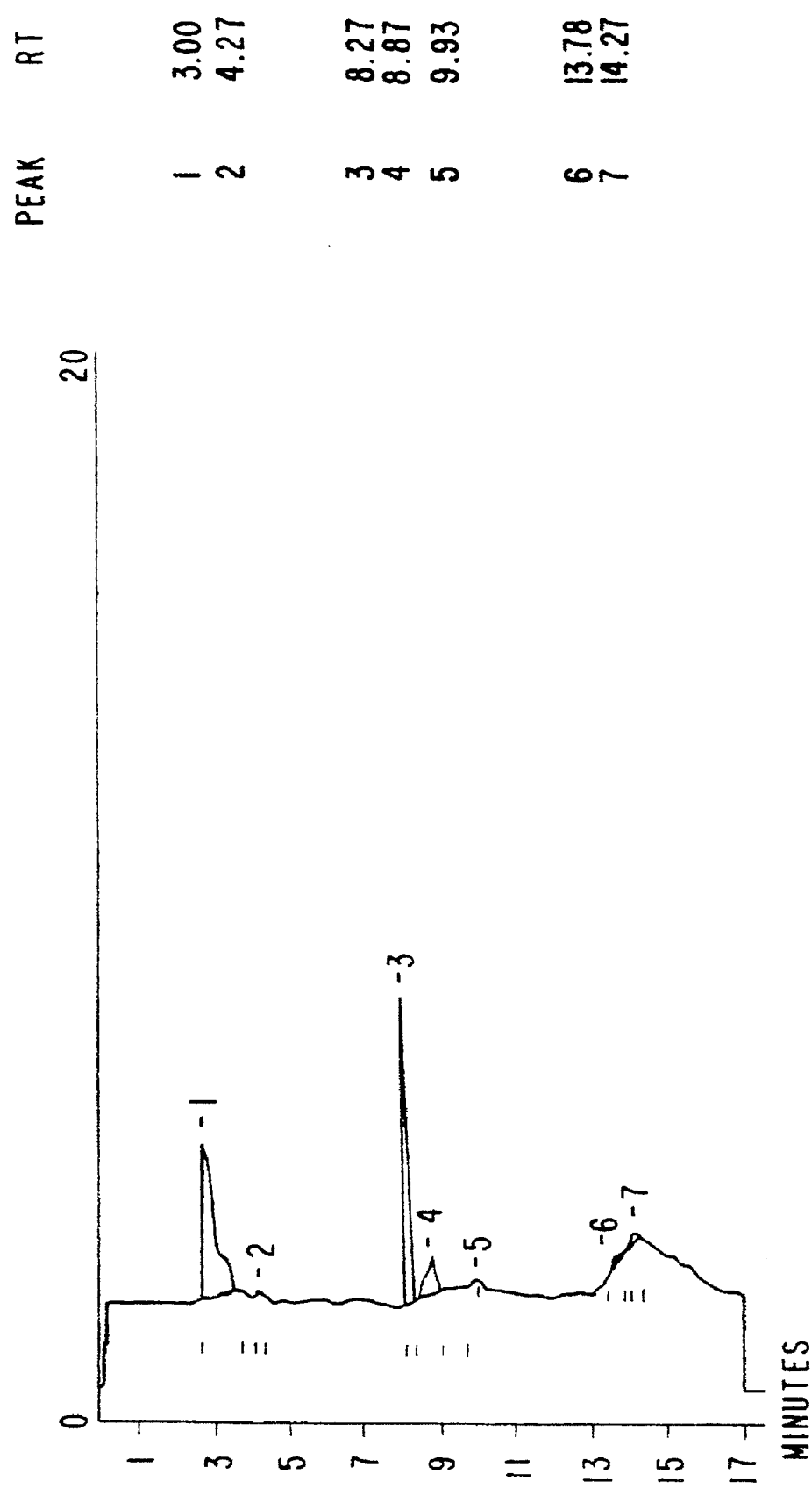
FIG. 1 is a High Performance Liquid Chromatography (HPLC) analysis of serum obtained from a healthy individual.

All patent applications, patents and literature references cited in this specification are hereby incorporated by reference in their entirety. In the case of inconsistencies, the present disclosure, including definitions, will prevail.

A novel compound, designated C-8.2, which can be isolated, detected, and/or quantitated (by non-limiting example) by HPLC, has been found to undergo acute changes in concentration shortly after HIV infection and can be employed in a method for identifying HIV-infected individuals.

"Shortly after HIV-infection" is defined herein as about 1–3 days after HIV infection.

C-8.2 has been found to be present in the serum of humans, pigs, cattle, rats, and mice and is believed to be a component of all mammalian serum.

"Blood fraction" is defined herein as serum or plasma.

Determination of either serum neopterin or β-2 microglobulin concentration has been proposed for the same purposes as the present invention. However, the methods described herein below differ from the experiments mentioned above in several ways: (1) the ultraviolet spectrum of C-8.2 does not contain the characteristic absorption of the pteridine ring characteristic of neopterin; (2) the infrared spectrum of C-8.2 is not consistent with the presence of a pteridine ring (3) the neopterin concentration does not change within days of exposure to HIV as does the C-8.2 concentration, and (4) β-2 microglobulin is a protein and has different solubility and physical properties when compared to C-8.2. In contrast, C-8.2 has been identified as a phospholipid or a mixture of related phospholipids by isolation and comparison with authentic materials by Fourier Transform Infrared (FTIR) spectroscopy, ultraviolet (UV) spectroscopy, Fast Atom Bombardment-Mass Spectroscopy (FAB-MS), and HPLC retention time as described below. Thus, C-8.2 is different both from β-2 microglobulin, which is a protein, and from neopterin, which is a pteridine metabolite. Because neither the β-2 microglobulin nor neopterin concentration responds rapidly to the initiation of HIV infection, neither measurement can be used for identifying HIV-infected individuals in like manner to C-8.2 measurement. Thus, the method disclosed herein for measuring C-8.2 levels as a diagnostic indicator for HIV infection could not have been anticipated by a knowledge of the current state of the art.

Throughout the specification, the marker compound of the present invention has been designated as "C-8.2". The present inventor has now unexpectedly discovered that C-8.2 is sphingomyelin and its derivatives. Derivatives of sphingomyelin include without limitation ceramides (sphingomyelin without the phosphocholine group) and sphingosyl-phospho-choline (sphingomyelin without the acyl amide group). Both C-8.2 and sphingomyelin will be used interchangeably throughout the specification.

In order to determine the HIV-infection status of a mammal, the concentration of C-8.2 is determined from blood, plasma or preferably serum. Determination of the levels of C-8.2 can be accomplished by HPLC, by ligand-based technologies, or by other specific methods known to those of ordinary skill in the art. In each case, the actual concentration determined is compared to the normal range for the age (or species) of the individual. Statistically significant values either above or below the normal range are diagnostic of HIV-infected individuals.

The present inventor has found that the amount of detectable C-8.2 varies according to the age of the individual. When practicing the methods of the present invention, the amounts of C-8.2 present in a sample are compared to an age-matched control group. The controls can be broadly grouped as follows: 0 (newborn)–23 months of age; 2 years of age–17 years of age; and 18 and over.

The uniqueness of the invention is not the particular method for determining C-8.2 concentration but the recognition that C-8.2 concentration is altered early in the course of infection with HIV and thus that the determination of C-8.2 levels, when compared to normal levels obtained by any technique, can be used to recognize individuals with HIV infection.

It should be understood that when analyzing serum from non-humans, both HIV and comparable viruses to HIV specific for that species will cause the same perturbations in C-8.2 concentration as has been found in humans infected with HIV. For example, Simian Immunodeficiency Virus (SIV) infection of primates (e.g. monkeys) can be detected using the same methods described below for HIV in humans.

C-8.2 refers to the peak detected by High Performance Liquid Chromatography (HPLC) using an acetonitrile gradient as the eluant at an elution time of 8.2 minutes after injection of the extracted serum sample into the column. It is the major peak present in the chromatogram. C-8.2 has the following physical properties: it is a phospholipid or mixture of related phospholipids, has a retention time of about 8.2 minutes when chromatographed on an amino carbohydrate column using an acetonitrile gradient and absorbs light at 210 nm and shorter wavelengths. As shown below in Example 4, C-8.2 has been identified as sphingomyelin and its derivatives. These physical properties confirm its identity.

Using the method of the present invention, a positive diagnosis of HIV infection is made when the levels of C-8.2 are substantially higher or lower (also referred to herein as statistically different) than those determined in age (and species)-matched control groups. "Substantially higher or lower" or "statistically different" levels of C-8.2 are defined herein as three standard deviations above or below the mean of those determined in healthy (non-HIV-infected) controls. Such standard deviations can be obtained using statistical methods well-known to those of ordinary skill in the art. The controls do not necessarily have to be performed simultaneously with every assay. A normal (control) range can be determined once for each patient population or group (as disclosed above) and the results of each assay compared to the values determined.

Using the method of the present invention a blood fraction, serum, for example, is obtained from a patient suspected of being infected by HIV. The minimum amount of serum needed for this analysis is 0.10 ml. The serum is extracted with an organic solvent, such as methanol, ethanol, tetrahydrofuran, chloroform or preferably acetonitrile at a ratio of between about 2 and 5 to 1 (organic solvent: serum) and preferably 4:1. The extract is centrifuged to resolve an organic and aqueous phase, for example 750×g for about 5 minutes at between about 2° C. and about 4° C. The organic layer is saved and contains C-8.2.

The amount of C-8.2 is then determined from the above mentioned organic phase, by non-limiting example, by HPLC analysis or preferably, antibody-based assays such as those described in Example 2 below. Antibody-based assays are preferred due to their ease of performance and the fact that sophisticated equipment is not required.

Many methods for the utilization of a specific antibody and tracer for the quantitation of a ligand have been developed. For radioimmunoassay, dextran-coated charcoal may be used to absorb unbound tracer, thus permitting determination of the bound fraction. Alternatively, (a) the bound fraction may be collected by binding to a second antibody (specific for IgG), either in solution or chemically bound to beads; (b) polyethylene glycol or ammonium sulfate may be added to enhance separation of bound and free tracer; or (c) coated tube methodology could be applied to permit separation of bound and free tracer. In addition to radioimmunoassay, the amount of phospholipid may be determined by Immunoradiometric assay (IRMA) (Miles, L. E. M., et al. Lancet. 2: 492, 1968), enzyme immunoassay (EIA) (Berry, N. J. et al., J. Virol. Met. 34: 91–100, 1991), and ELISA (Engvall, E. et al., G. Immunochemistry 8: 871, 1971), and any other ligand assay technique known to those of ordinary skill in the art.

Suitable HPLC columns for use in the present invention include Adsorbosphere - $NH_2$ (Alltech, Chicago, Ill.) Econosil - $NH_2$ (Alltech), devitalized polydextran beads, such as Lichrosorb - $NH_2$ (Alltech), SEPHADEX™-LH20 (Pharmacia, Piscataway, N.J.) and preferably an Amino Carbohydrate column (Alltech). The chromatographs are compared with age (and species, where applicable)-matched controls. Any value 3 standard deviations above or below the control values is indicative of a positive diagnosis of HIV infection.

The solvent to be used with each of the above HPLC columns can be optimized for C-8.2 detection and quantitation. For example, when employing an Amino Carbohydrate column, a complex gradient can be used such as t=0 minutes (time post injection of the sample into the column), 95% acetonitrile; t=2 minutes, 75% acetonitrile; t=10 minutes, 55% acetonitrile; t=12 minutes, 40% acetonitrile; t=14 minutes and t=15 minutes, 95% acetonitrile (elution). When employing the other HPLC columns disclosed above or any other equivalent affinity column, such binding, washing and elution gradients can be determined by routine experimentation well-known to those of ordinary skill in the art based on the physical properties of C-8.2 disclosed herein.

As described below, the C-8.2 levels determined in HIV-infected individuals were found to return to normal upon the initiation of AZT ddI or ddC therapy only when such therapy was effective. As described below four HIV-infected children, ages 4–11 years, had neurological dysfunctions typical of HIV infection. All of the infected children had statistically significantly elevated levels of C-8.2 in their serum as determined by HPLC analysis. All the children were given AZT in order to control disease symptoms. AZT therapy was ineffective in all four children and the levels of C-8.2 didn't change. However, in eight age-matched children who were also HIV-infected and received AZT and benefitted from the treatment, C-8.2 levels returned to the normal range. Therefore, determination of C-8.2 levels can be used to monitor the efficacy of anti-HIV therapeutic agents.

When used to monitor efficacy of antiretroviral drug treatment using, for example, AZT, ddI, ddC or mixtures thereof, C-8.2 levels can be monitored during or after the institution of such therapy. These levels can be compared to the levels determined before therapy has started. Therefore, if the C-8.2 levels do not return to those obtained for age-matched control groups, therapy may be discontinued. This is a most important finding because all anti-HIV theraputics are highly toxic and if they are not effective they should be discontinued as soon as possible.

The method of preparing serum extracts for analysis is suitable for blood or plasma. Larger or smaller volumes can be used as long as the relative proportions disclosed above are maintained. Because of the specific hazard of HIV transmission, it should be presumed that all human materials are from HIV-infected patients and the handling of blood or tissue specimens should be performed with great care.

In addition to its utility as a marker of HIV infection, the identification of the abnormal regulation of C-8.2 levels and its temporal relation to infection by the virus suggests that it may be used as a surrogate end point or measurement of the health or infection status of a patient to evaluate therapy.

Without wishing to be bound by theory, it is believed that for the levels of C-8.2 to change so rapidly as one of the early events after HIV infection, there should be a C-8.2-specific hydrolytic or synthetic enzyme whose activity is altered upon HIV infection. The postulated enzyme could be part of the process whereby the cell machinery is subverted by the virus. Blocking of the process may prevent the virus from controlling cellular functions. As such, the recognition of the existence of such an enzyme can be used to identify a possible new target for HIV-specific chemotherapy.

The assays of the present invention are based on alterations in the levels of C-8.2 and not on antigenic properties of the virus. Therefore, infection by all Human Immunodeficiency Viruses (HIV-1, HIV-2, etc.) will be detectable using these assays, as will any other antigenic variants thereof. Indeed, one of the advantages of the method for detecting HIV infection of the present invention is its ability to detect all HIV irrespective of their antigenic makeup. This is a distinct advantage because HIV has been found to be highly mutagenic. As the virus changes, no new reagents will be required to practice the methods of the present invention.

HIV is not stable in organic solvents. The solvent extraction method described above (a) inactivates free HIV particles and (b) destroys HIV-infected cells. These are the agents by which HIV is transmitted. Thus, the use of this step reduces the hazard to the technologist performing the assay.

Figure 8:
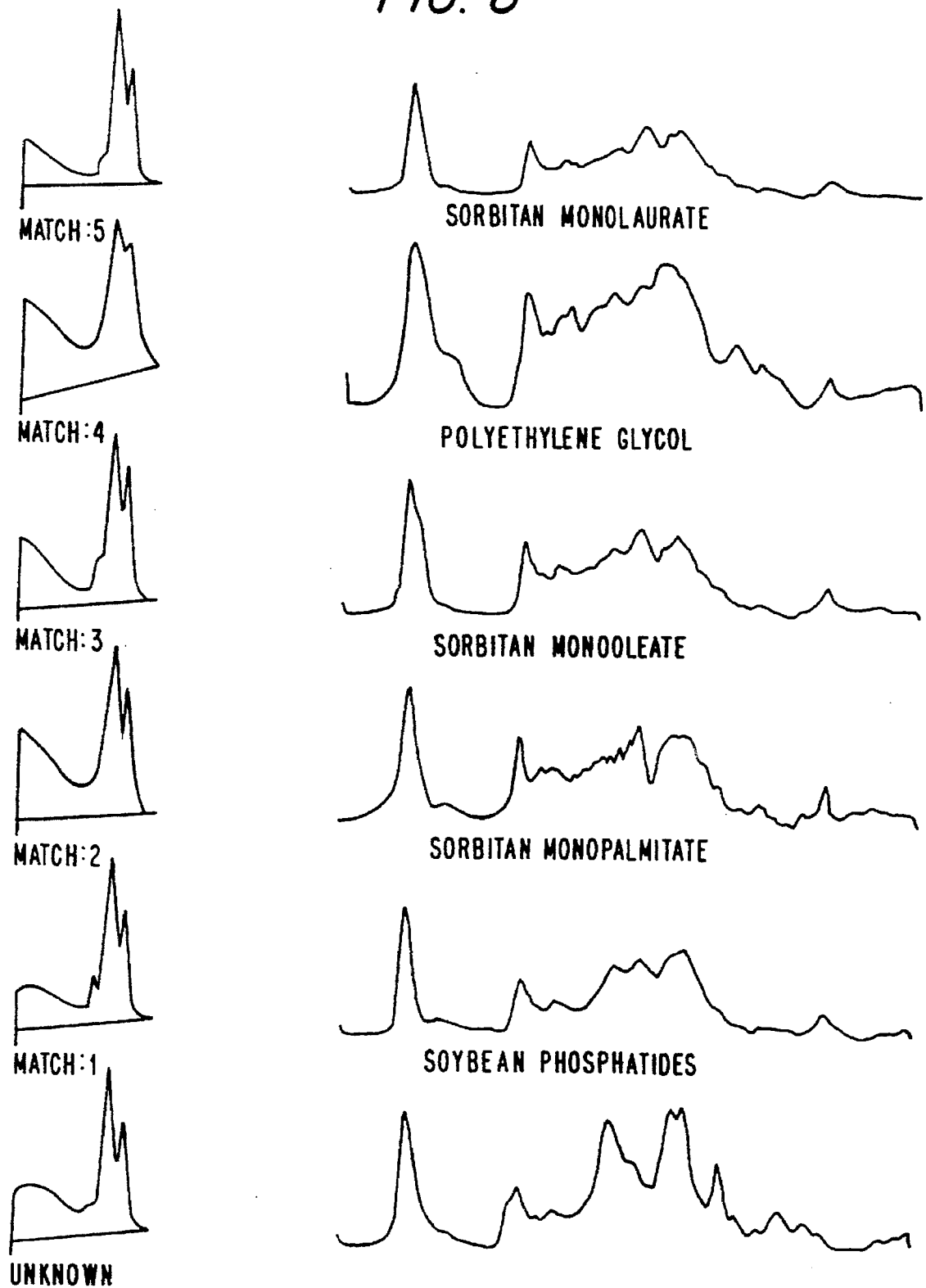
FIG. 8 is an FTIR analysis of lipid standards.
Figure 9:
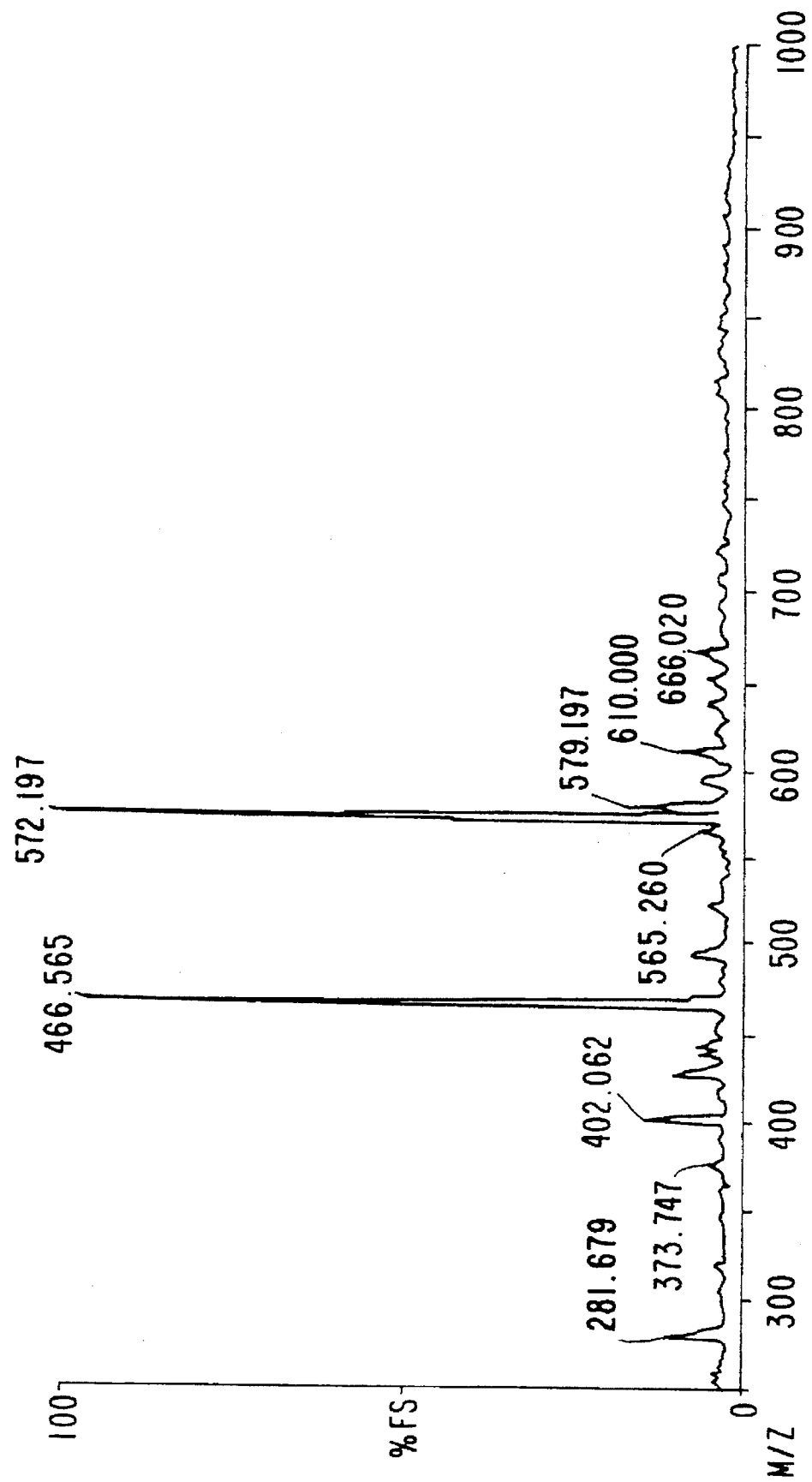
FIG. 9 is a Fast Atom Bombardment Mass Spectroscopy (FAB-MS) analysis of fraction 24 obtained from an amino carbohydrate HPLC column in accordance with the methods of present invention.

C-8.2 is believed to be a phospholipid or mixture of related phospholipids based upon the FTIR shown in FIG. 8 (a and b) because the specific bands in the lipid standards shown in FIG. 9 are also present in C-8.2.

The first example below will describe the use of HPLC for the rapid determination of C-8.2 concentrations. The second example will describe the production of ligand-specific materials and methods for C-8.2 detection. The third example will describe the preliminary characterization of C-8.2 obtained from normal adults.

The present invention is further described below in specific working examples which are intended to further illustrate the invention without limiting its scope.

EXAMPLE 1

Determination of C-8.2 Levels by HPLC

Serum (0.1 ml) was extracted with acetonitrile (0.4 ml) in a glass tube (12×75 mm) at room temperature. The extract was centrifuged at 2°–4° C. for 5 minutes at 750×g. The extract was removed with a 1 ml syringe, the syringe attached to a filter (0.45 microns, LC13 Acrodisk, Gelman Laboratories, Ann Arbor, Mich.) and the extract filtered. The filtrate was collected in a suitable glass vial. If desired the vial may be an HPLC autosampler vial that matches the HPLC autosampler if one is used.

HPLC Analysis:

The method for HPLC (Model 401T, BioRad, Richmond, Calif.) analysis is based on the use of an amino carbohydrate column (4.6×250 mm; Alltech, Chicago, Ill.). Samples were eluted with a complex gradient using mixtures of acetonitrile and water: (1) t=0 minutes, 95% acetonitrile; (2) t=2 minutes, 75% acetonitrile; (3) t=10 minutes, 55% acetonitrile; (4) t=12 minutes, 40% acetonitrile; (5) t=14 minutes, 40% acetonitrile; (6) t=15 minutes, 95% acetonitrile. Eluted materials from the chromatogram were detected by monitoring ultraviolet absorbance at 210 nm. Peak areas and heights were determined with a computer software package (BioRad). Both height and area (in area integration units—AU) were proportional to the amount of extract injected. Normal values may be determined with either parameter.

Results: Adults

Serum was obtained from normal (non-HIV-infected) adults, extracted and chromatographed as described above. Serum concentrations of C-8.2 in normal adults of both sexes (n=14) had an approximately normal distribution with a mean of 38 area units (AU) and a standard deviation of 3.5 AU. Samples were scored as normal if they were within the range of 27 to 48 AU and abnormal if they were not within three standard deviations, 10.5 AU, within this range (a representative chromatogram is shown in FIG. 1). Based on a normal distribution, 99% of samples should be within this range. Abnormal samples can be lower or higher than the normal range.

Figure 2:
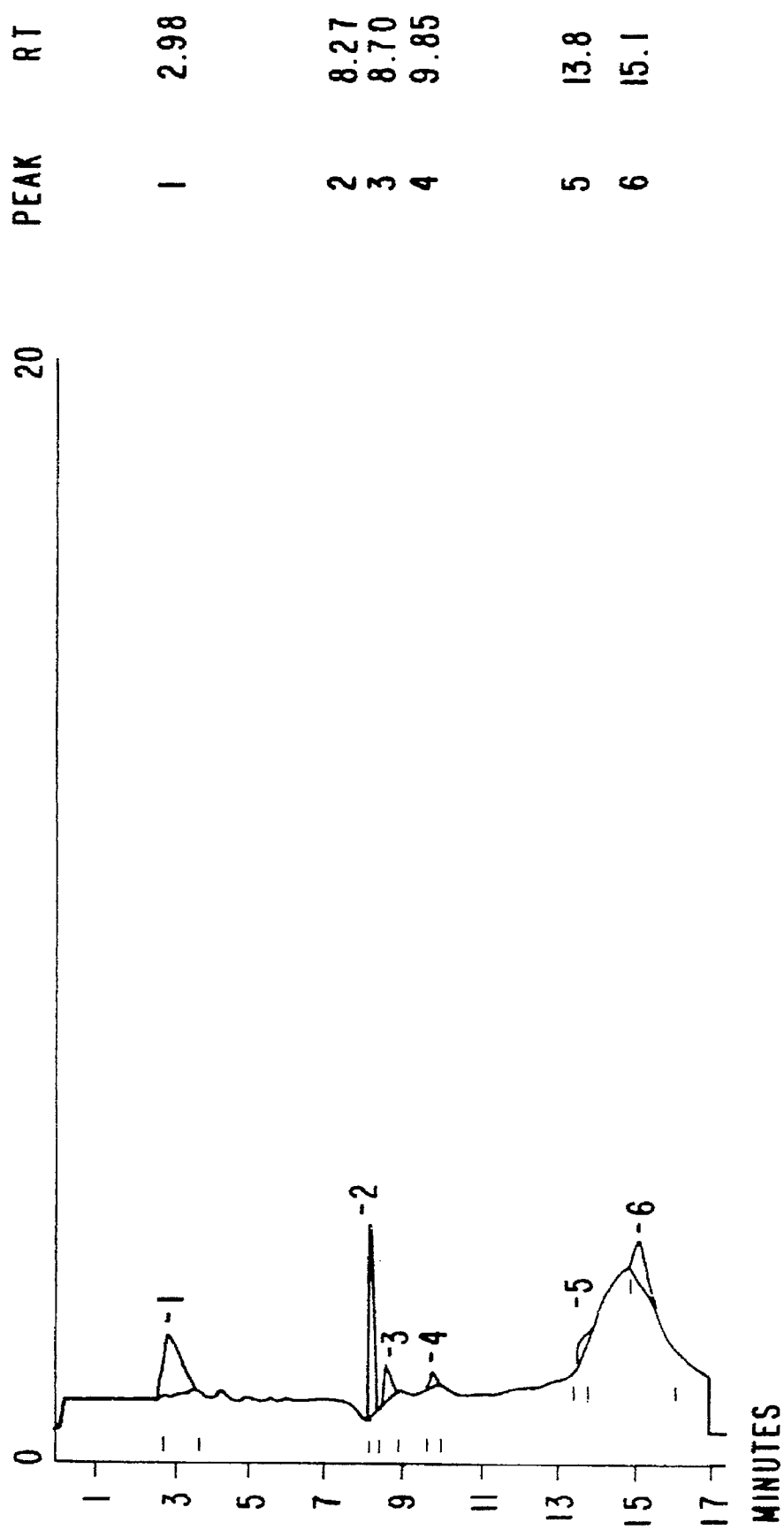
FIG. 2 is an HPLC analysis of serum obtained from an HIV-infected patient with low C-8.2 levels.
Figure 3:
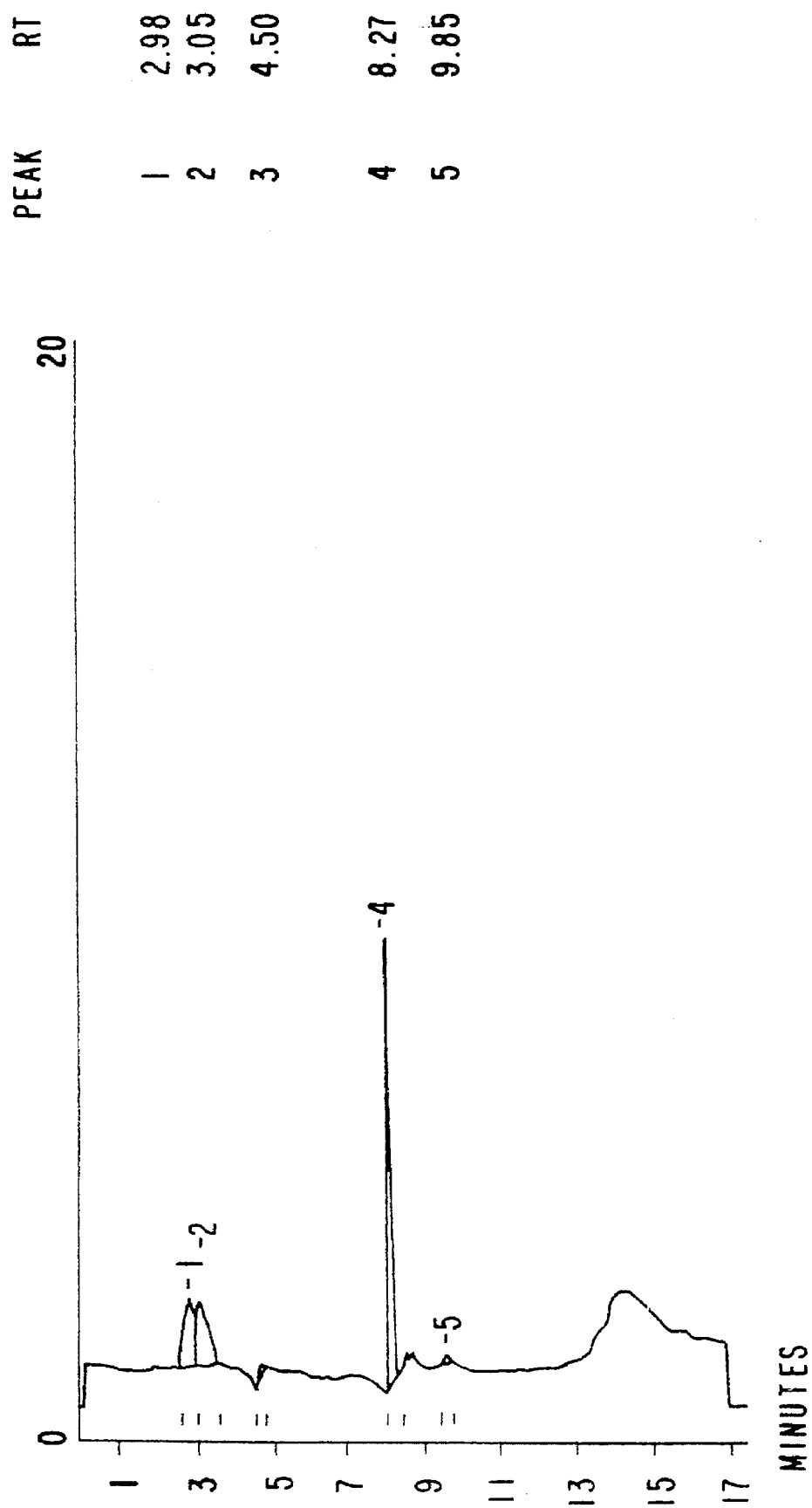
FIG. 3 is an HPLC analysis of serum obtained from an HIV-infected patient with high C-8.2 levels.

C-8.2 in serum from adults with a known HIV infection (n=19), as shown by presence of HIV-specific antibodies, ranged from 5 to 65 AU with a mean of 38 AU; there were few samples within the normal range (n=3) and the values were not normally distributed (representative chromatograms are shown in FIG. 2 and FIG. 3) The box below shows the correlation of HIV status as determined by specific enzyme immunoassay, with scores for C-8.2 within 3 standard deviations the normal range and not within three standard deviations the normal range.

First Group:

| HIV by HPLC | HIV antibodies detected by EIA | |
|---|---|---|
| | NEGc | POS$_d$ |
| NEG[a] | 14 | 3 |
| POS[b] | 0 | 16 |
| [1]$X^2 = 22.9$; $p < 0.0001$ | | |

[a]C-8.2 concentration determined by HPLC within the range 27 to 48
[b]C-8.2 concentration not within range 27 to 48 AU
c-HIV negative serum when tested by EIA
[d]HIV positive serum when tested by EIA
[1] Chi Square.

Therefore, the above results show that the method of the present invention was able to identify 16 out of 19 HIV-infected individuals. It remains to be seen if the 3 antibody positive patients with normal C-8.2 levels actually develop AIDS at a later date.

Second Group:

The samples tested (n=37) were selected from samples obtained from adult individuals at a high risk for HIV infection (male homosexuals, intravenous drug abusers, or their sexual partners) and tested for the presence of HIV antibodies by a commercial blood bank. The C-8.2 levels ranged between 28 AU and 48 AU with a standard deviation of 3.5 AU.

| HIV by HPLC | HIV antibodies detected by EIA | |
|---|---|---|
| | NEG | POS |
| NEG | 13 | 4 |
| POS | 7 | 13 |
| $X^2 = 6.36$; $p < 0.01$ | | |

The above illustrates the general utility of the method of the present invention for identifying individuals infected with HIV.

Third Group:

Most serum samples (8 of 10) obtained from adults with HTLV 1 or 2 infection (n=10) were within the normal range of the samples[2]. Of the 2 samples that had C-8.2 levels out of the normal range, one tested positive for HIV by EIA; the other did not, but there was no further follow-up possible to determine if the patient was in the time period after infection but prior to development of antibodies. The data illustrates that the change in C-8.2 concentration is specific for HIV rather than for other types of related human T-cell lymphotrophic viruses.

[2] The normal control range of values of C-8.2 should range between about 28 AU and about 48 AU for this patient population with a standard deviation of 3.5 AU.

Fourth Group:

Two sero-conversion panels with twice weekly samples were tested as shown in the box below. The samples were obtained from two adults who had unidentified "high risk" events and agreed to provide serum samples twice a week. In each case the first sample was obtained within 48 hours of the event (no other information about the nature or timing of the event was made available in order to preserve confidentiality). Normal C-8.2 levels for these patients should be between 28 AU and 48 AU with a standard deviation of 3.5 AU. The results are set forth in Table 1 below.

TABLE 1

| | | C-8.2 Level | | HIV-specific Antibodies | |
|---|---|---|---|---|---|
| Sample # | Day # | Patient 1 | Patient 2 | Patient 1 | Patient 2 |
| 1 | 1 | 25.5 | 25.1 | 0 | 0 |
| 2 | 4 | 19.8 | 15.0 | 0 | 0 |
| 3 | 7 | 23.5 | 23.4 | + | 0 |
| 4 | 10 | 24.5 | — | ++ | 0 |
| 5 | 14 | 26.2 | 16.1 | +++ | 0 |
| 6 | 17 | 30.0 | 15.0 | +++ | 0 |
| 7 | 21 | 24.3 | 14.8 | +++ | 0 |
| 8 | 24 | 25.2 | — | +++ | 0 |

In both individuals, the initial concentration of C-8.2 (on day 1) was already three standard deviations below the normal range and therefore diagnostic of HIV infection. In the first patient, when HIV-specific antibodies developed, the C-8.2 level returned towards normal but that value was not sustained as the infection progressed. In the second patient, HIV-specific antibodies did not develop for several months and no rebound in C-8.2 level was observed. In both patients, the change in C-8.2 level occurred prior to the development of HIV-specific antibodies.

These data illustrate the utility of C-8.2 level determination for recognizing HIV-infected individuals within 3 days of a high risk event that might lead to HIV transmission.

Results: Infants With HIV Antibodies

Group 1: Normal Infants

Figure 4:
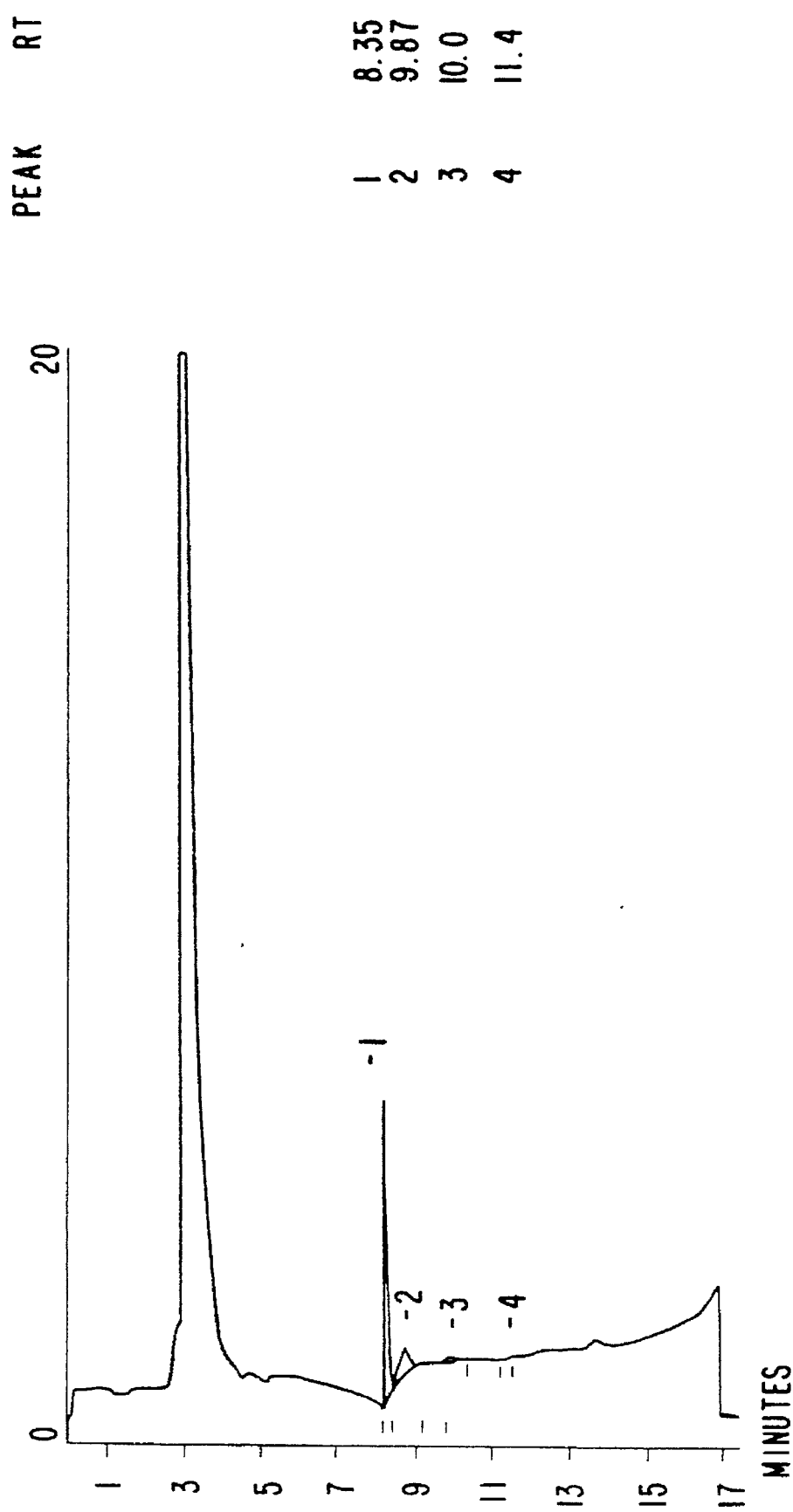
FIG. 4 is an HPLC analysis of C-8.2 levels obtained from a non-HIV infected newborn infant born to an HIV-infected mother.

C-8.2 levels in normal (non-HIV-infected) infants (ages 8 days to 15 months) ranged from 18 to 33 AU (n=11) with a mean of 25.5 and a standard deviation of 2.5 AU. This sets the normal range for comparison with the infants at high risk for HIV infection. A representative chromatogram is shown in FIG. 4.

Group 2: Infants Less Than 18 Months Of Age At High Risk For HIV Infection

Figure 5:
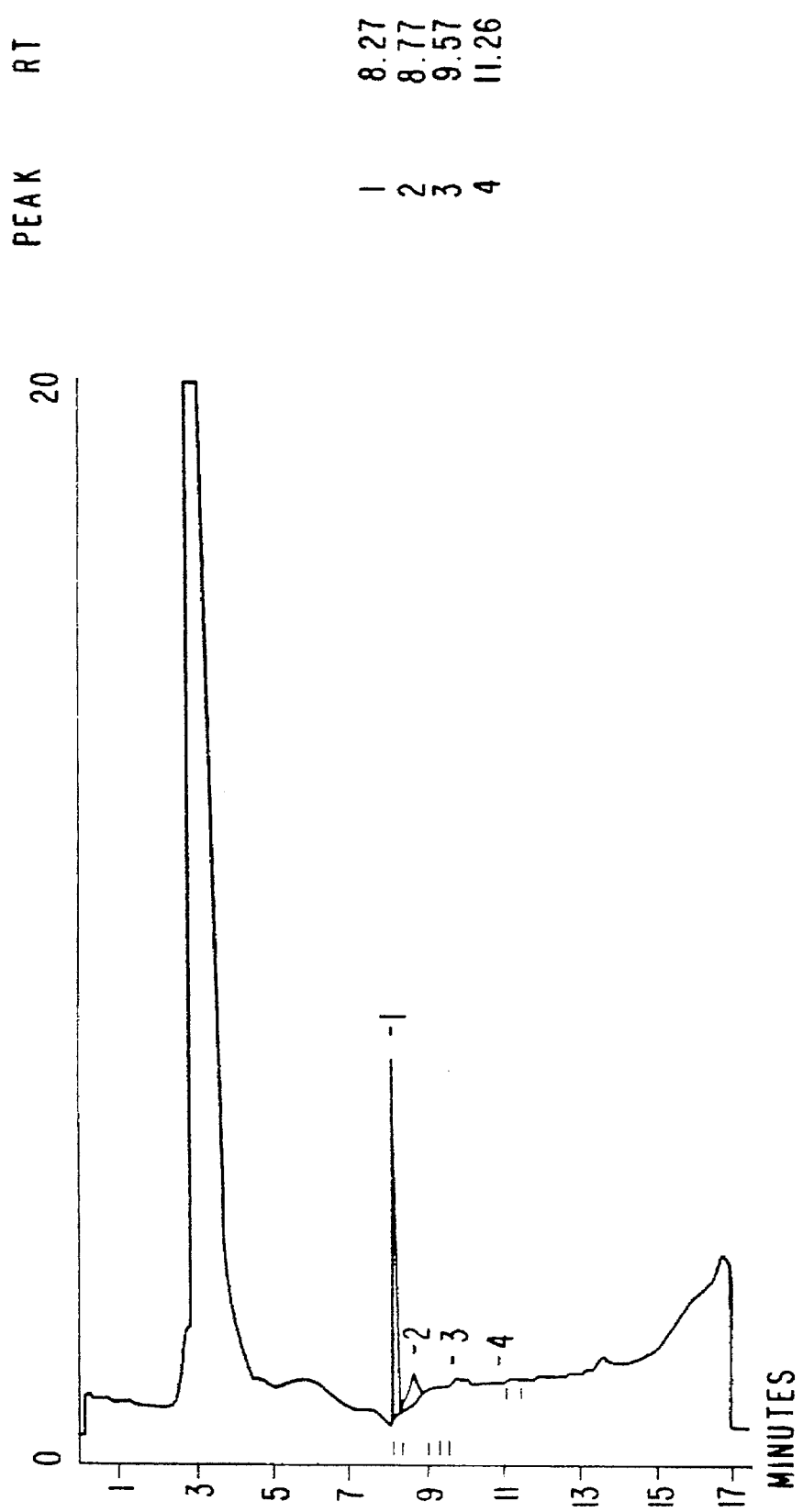
FIG. 5 is an HPLC analysis of C-8.2 levels obtained from an HIV-infected newborn infant born to an HIV-infected mother.

In serum from high-risk infants (born to HIV-infected mothers) less than 18 months of age (n=27) with HIV-specific antibodies at birth, levels of C-8.2 were within the normal range in 15 and were out of the normal range in 12. None of the children with C-8.2 values within the normal range had symptoms of HIV infection, while 9 of 12 of the infants out of the normal range had clinical signs of HIV infection, including lymphadenopathy. The final diagnosis of the remaining 3 is not yet known because of their age, although they continue to have HIV specific antibodies in their serum. A typical chromatogram is shown in FIG. 5. The data are tabulated below.

| Infants less than 18 months of age at high risk for HIV infection C-8.2 Level Determined by HPLC | | |
|---|---|---|
| | No symptoms | Symptoms |
| Normal[a] | 15 | 0 |
| Abnormal[b] | 3 | 9 |
| $X^2 = 16.9; P < 0.001$ | | |

Notes:
[a] C-8.2 concentration within the range 18 to 33 AU
[b] C-8.2 concentration either three standard deviations below or above 33 AU

Group 3: Older Infants And Children

In older infants and children, aged 2 years to 11 years, C-8.2 concentrations were statistically significantly elevated (i.e. at least 3 standard deviations) in all (n=4) HIV-infected subjects untreated with AZT (results not shown). In AZT-treated individuals (n=16), C-8.2 was within the normal range in 5 subjects and elevated in 11 subjects (results not shown). The latter group continued to have neurological and behavioral disorders and other neurological symptoms typical of HIV infections, whereas the group with normal values did not have such disorders. Importantly, in 2 children, sequential samples showed a high C-8.2 level prior to AZT therapy which decreased to the normal range within a month of the start of treatment.

In summary, C-8.2 determination in infants with HIV-specific antibodies discriminated between those infants with antibodies of maternal origin from those infected with HIV. Secondly, C-8.2 levels were a marker for the effectiveness of AZT therapy.

Evaluating C-8.2 Levels for Monitoring the Efficacy of Antiretroviral Drug Therapy Four HIV-infected children, ages 4–11 years had neurological symptoms typical of HIV infection. Their serum levels of C-8.2 were significantly elevated (40, 41, 44 and 46 AU) when compared to age-matched controls (20–33 AU, N=11). AZT therapy was instituted but was not effective in reducing the disease symptoms and C-8.2 levels didn't change in these patients. However in 8 HIV-infected children with C-8.2 levels significantly different from control values receiving the same AZT treatment who benefitted from AZT, C-8.2 levels returned to normal ranges (24–34 AU).

In addition, a four year old child who was HIV antibody negative, as tested by ELISA and Western Blot, was examined. The C-8.2 levels were 41 AU. The child was symptomatic for HIV infection and could be diagnosed as HIV positive using the methods of the present invention.

EXAMPLE 2

Development Of Reagents For Ligand Assays
Method For Generation Of C-8.2 As A Hapten Linked To Carrier Protein Described below are methods for the preparation of reagents for ligand based assays for quantitating C-8.2.

The fatty acid side-chain of C-8.2 contains several alkene groups. These alkene groups add iodine or other halogens across the alkene bond. The resulting iodine can be displaced with mercaptoacetic acid (Aldrich, Milwaukee, Wis., cat. number M310-8) or 3-mercaptopropionic acid (Aldrich, cat. number M580-11). The difference between the two reagents will be the length of the spacer chain between the carrier and the hapten. Longer spacer chains may also be used. The products may be purified by chromatography on a DEAE derivative of a polydextran bead such as SEPHADEX™ A-50 (Pharmacia, Piscataway, N.J.) with acetonitrile/water (1:1) as the eluant, derivatized polydextran beads such as SEPHADEX™ LH-20 (Pharmacia) with methanol as the eluant, and finally with SEPHADEX™ a polydextran molecular sieve column such as G-10 (Pharmacia) with water as the eluant. The C-8.2 used as the starting material may be isolated from normal plasma. The thioglycolate derivative of C-8.2 may be coupled to Bovine Serum Albumin (BSA) with EDC (1-ethyl-3-(3-dimethylaminopropyl) carbodiimide hydrochloride). Alternately, a complete kit for coupling the resulting product to thioglycolate can be used (Pierce, Rockford, Ill.; cat #77101 A).

The above conjugates can be used to raise specific antibodies directed against C-8.2. These antibodies can be either polyclonal (Lieberman, S. et al., *Recent Progress in Hormone Research* 15: 165–200, 1959) or monoclonal (Blethen, S. L. et al., *J. Ped. Endocrin* 3: 217–223 (1989).

Methods For Preparation Of A Tracer

A method for the labeling of phospholipids has been published (Anthonov P. A. Panmcheva R. P., Ivanov I. G. *Biochem. Biophys. Acta* 835: 408–410, 1985). In this method, 1 mCi of Na [$^{125}$I] (Dupont, Boston, Mass.) in 10 μl of water is mixed with 10 μl of 0.3M sodium acetate, pH 4.5 and 10 μl of freshly prepared 3.0 mM TlCl$_3$. The volume is adjusted to 100 μl. The mixture is allowed to react for 5 minutes and 10–15 mg of C-8.2 is added as a solution (0.5 to 1.0 ml) in chloroform/methanol (1:1). The mixture is allowed to incubate at room temperature for 10 to 15 minutes. The reaction is quenched by the addition of 3 ml of chloroform and 5 ml of 20 mM Na$_2$S$_2$O$_3$. The mixture is vortexed and centrifuged at 250×g for 5 minutes. The lower, organic layer will contain the lipids. The lipid product is washed twice with 5 ml of 20 mM Na$_2$S$_2$O$_3$. The chloroform extract is evaporated to dryness and purified by thin layer chromatography (Whatman, Alltech, Chicago, Ill.) or a derivatized polydextran beads such as SEPHADEX™ LH-20 column chromatography. The final product will have a specific activity of about 10 μCi per mg of phospholipid.

Alternatively, the reaction can be catalyzed by Chloramine T (Pierce Chemicals) as follows. In this method, 1 mCi of Na[$^{125}$I] (DuPont, Boston, Mass.) in 10 μl of water is mixed with 10 μl of 0.1M phosphate buffer, pH 7.2. Chloramine T (10 μl of a 20 mM solution) is added and the volume adjusted to 100 μl. The reaction and purification will be carried out as described above.

An enzymatic method of catalyzing the introduction of iodine into phospholipids has also been reported (Benenson A. Mersel M. Pinson A., and Heller, M. *Anal. Biochem.* 101: 507–512, 1980). In this procedure, the specific phospholipid is subjected to ultrasonic radiation in Ca-Mg-free Phosphate-Buffered-Saline (PBS, pH=7.4). To the phospholipid is added 100 μl of 0.1 mCi carrier-free [$^{125}$I] (DuPont, Boston, Mass.), 50 μl of lactoperoxidase (0.25–2.5 μg, BioRad, Richmond, Calif.), 50 μl of 300 μU glucose oxidase (BioRad) and 250 moles of glucose in 50 μl. The mixture is incubated at room temperature for 15 min. The reaction is quenched by the addition of 10 μl of 6.6 mM thiosulfate (Fisher Chemicals, Springfield, N.J.) and the product purified as above.

Methods For Utilization Of Antibody And Tracer

A typical antibody-based assay may be performed as follows:

1. Initial detection and titration of antibody:

Sera from rabbits immunized with C-8.2-BSA conjugates (or monoclonal antibody containing media or fluid) is serially diluted with bovine serum albumin (BSA) in phosphate buffered saline, pH=7.4. The tracer, as prepared above, is diluted with the same buffer to a concentration of 40,000 to 125,000 CPM/ml. The serial dilutions are pipeted into 12×75 mm glass tubes and incubated with the tracer (0.4 ml) for 1 hour at 37° C. At the end of the incubation, the tubes are placed in the refrigerator (2° to 4° C.) for 20 minutes. Rabbit IgG specific Immuno-beads are added. (Bio-Rad, Richmond, Calif.) (If monoclonal antibodies used, then the Immuno-beads should be specific for mouse IgG.) Each tube is vortexed and allowed to incubate for 1 hour in the refrigerator at 2°–4° C. At the conclusion of the second incubation, the tubes are centrifuged in a refrigerated centrifuge at 2000×g for 20 minutes and the supernatant discarded without disturbing the pellet. Each tube is then counted in a gamma counter (LKB, Gaithersburg, Md.). The initial dilution of antibody to use for assay is the dilution that produces half-maximal amount of binding. For the most sera obtained after suitable immunization, the active dilution to be used ranges from 1/1,000 to 1/50,000, for a final dilution of 10,000 to 500,000 per ml of serum. After establishment of the standard curve, the final dilution for the antibody is further modified to control the sensitivity, as described below.

2. Establishment of standard curves

Pure C-8.2 (as isolated in Example 3 below) is diluted with BSA containing phosphate buffered saline and used to generate a standard curve. The actual amount used for each standard is confirmed by the HPLC method (Example 1). The range of the standard curve is established based on the normal values obtained using the method of Example 1. Standard 4 has the mean amount of C-8.2 detected in the control population. Standard 2 and 6 have 3 standard deviations less or more, respectively, than the mean amount detected in the control population. The concentration in the remaining standards are selected to maintain geometric proportion. The final antibody dilution is adjusted such that standard 4 displaces 50% of maximum binding (Bo) as measured in tubes 5,6. The specific activity of the tracer is adjusted (lowered) by addition of unlabeled material to adjust the slope of the standard curve to satisfy these parameters.

3. Assay Protocol

| Tube # | Description | Comments |
|---|---|---|
| 1,2 | Non-Specific Binding | No Antibody |
| 3,4 | Total | Tracer only, reserve for counting |
| 5,6 | Maximum binding (Bo) | Antibody and Tracer (A + T) |
| 7,8 | Std. 1 (10 μl) | |
| 9,10 | Std. 2 (10 μl) | |
| 11,12 | Std. 3 (10 μl) | |
| 13,14 | Std. 4 (10 μl) | |
| 15,16 | Std. 5 (10 μl) | |
| 17,18 | Std. 6 (10 μl) | |
| 19,20 | Std. 7 (10 μl) | |
| 21,22 | QC - 1 (10 μl) | Value established as low end cut-off |
| 23,24 | QC - 2 (10 μl) | Value established as expected mean |
| 25,26 | QC - 3 (10 μl) | Value established as high end cut-off |
| 27,28 | Unknown (10 μl) | From individuals to be tested |
| etc. | | Additional tubes as needed | i. Label tubes for the above protocol.

ii. Piper 10 μl of each standard, control and unknown into the appropriate pair of tubes.

iii. Add 400 μl of tracer to each tube with a repeating pipet. Put aside tubes 3 and 4; they are ready for counting.

iv. To tubes 1 and 2, add 100 μl of phosphate buffered saline with BSA, pH=7.4.

v. Starting with tube no. 5 above, add 100 μl of antibody diluted as above to each tube.

vi. Vortex all tubes. Incubate 1 hour at 37° C.

vii. Transfer all tubes to refrigerator (2° to 4° C.) and incubate for 30 minutes.

viii. Dissolve Immunobeads (20 mg) in 20 ml of phosphate buffered saline. Mix slowly on stirrer at 2° to 4° C. until needed.

ix. Add 100 μl of Immunobeads to each tube. Vortex. Incubate in refrigerator for 30 minutes.

x. Centrifuge tubes at 2000×g (3200 RPM) for 20 minutes at 2° to 4° C. (RT6000 B Dupont Centrifuge, Dover, Del.).

xi. Decant liquids without disturbing pellet. Count tubes in gamma counter.

4. Sample Preparation

All blood samples should be treated according to the OSHA blood borne pathogen standard. To prepare samples for assay, whole blood is centrifuged in a covered centrifuge for 5 minutes at 750×g. The clear serum is transferred to a suitably labeled glass tube, capped and stored frozen at −70° C. until assayed. At the time of assay, the sample is thawed at room temperature and vortexed carefully. No heat should be used in thawing. Samples must not be allowed to remain unfrozen for long periods.

5. Analysis of Results i. The standards are used to generate curves as for other RIA procedures (plot (a) counts bound vs. concentration, (b) bound counts vs. log of concentration, or (c) log of bound counts vs. log of concentration). Interpolate unknowns against the standard curve. The calculations can be performed by hand or computer as desired.

ii. Data sets are accepted as valid and results reported only when the QC samples are within the expected ranges.

iii. Diagnosis of HIV infection should be confirmed by alternate techniques, such as PCR or Western blot. In the event diagnosis cannot be confirmed by one of these techniques, additional samples should be obtained and assayed.

In addition to RIA, the concentration of C-8.2 in Serum can be determined with other assays based on specific antibodies (such as IRMA, EIA, or ELISA) or by other standard color development techniques, such as those used in clinical chemistry for the assay of cholesterol.

EXAMPLE 3

Characterization Of C-8.2 From Normal Individuals
Description Of Assay For Purification Quantification of the amount of C-8.2 in a particular fraction was performed by injection of an appropriate aliquot onto the HPLC column as described in Example 1 above. The peak area (in area units—AU), as determined by computer integration, is then multiplied by the dilution factor to determine the total amount of C-8.2 in AU.

Isolation Of C-8.2 From 1.5 Liters Of A Plasma Pool And Chemical Analysis

A plasma pool (1.5 L) obtained from normal, non-HIV infected adults, was extracted with 6 L of acetonitrile. The extract was filtered to remove denatured and insoluble materials. The extract was treated with 3.75 L of benzene and 2 phases formed: (1) the lower, aqueous phase -discarded- and (2) the upper, organic phase. The upper phase was evaporated to dryness, in batches, on a rotary evaporator (Buchler, purchased from Fisher, Springfield, N.J.) with the temperature of the water bath not exceeding 40° C. Each batch was dissolved in a limited amount of methanol and pooled with other methanolic extracts. The final pooled methanolic extract was reduced in volume to less than 10 ml.

The second step was chromatography derivatized polydextran beads such as on SEPHADEX™ LH-20 (Pharmacia, Piscataway, N.J.) with methanol as the solvent. C-8.2 was purified in 5 ml batches and corresponding fractions pooled. C-8.2 concentration of each fraction was monitored by HPLC. A representative chromatogram is shown in FIG. 4. Fractions containing C-8.2 were pooled and evaporated to dryness in a rated V-vial (Fisher, Springfield, N.J.) under a stream of dry nitrogen. The V-vival was weighed, partially purified C-8.2 was dissolved in a minimal volume of methanol and the amount of product determined by HPLC. The fractions with the largest peaks of C-8.2 had the smallest peaks of other materials. Because the wavelength measured was 210 nm and the contaminants absorbed light predominantly at other wavelengths, it was not possible to determine the actual degree of purification.

The fractions with the highest specific activity were fractions 9–11 with some C-8.2 also present in fractions 12–14. These side fractions of lower specific activity were reserved. Only the high specific activity fractions (9–11) were used for further purification.

The final step in purification of C-8.2 was preparative HPLC with an $NH_2$-Lichrosorb column (10×250 mm, Alltech). Material applied to column in 95% acetonitrile - 5% water. C-8.2 eluted at linear gradient to 40% acetonitrile - 60% water. A chromatogram with the same gradient as used for serum samples with a single peak at 8.2 minutes was obtained, indicating that the material seemed to be homogeneous by this criterion (data not shown).

Based on the specific activity (AU/mg) of C-8.2 isolated from 1.5 liters of a plasma pool from uninfected adults, the approximate concentration of C-8.2 was 100 mg/l or about 125 µM.

UV Analysis

The UV spectrum of C-8.2 were determined with a model lambda 3a UV/VIS spectrophotometer (Perkin-Elmer, South Plainfield, N.J.). The sample was prepared as follows: The material was prepared in 80% acetonitrile - 20% water. The same solution was used as the reference. This solvent mixture does not absorb light with wavelengths longer than 200 nm.

Figure 6:
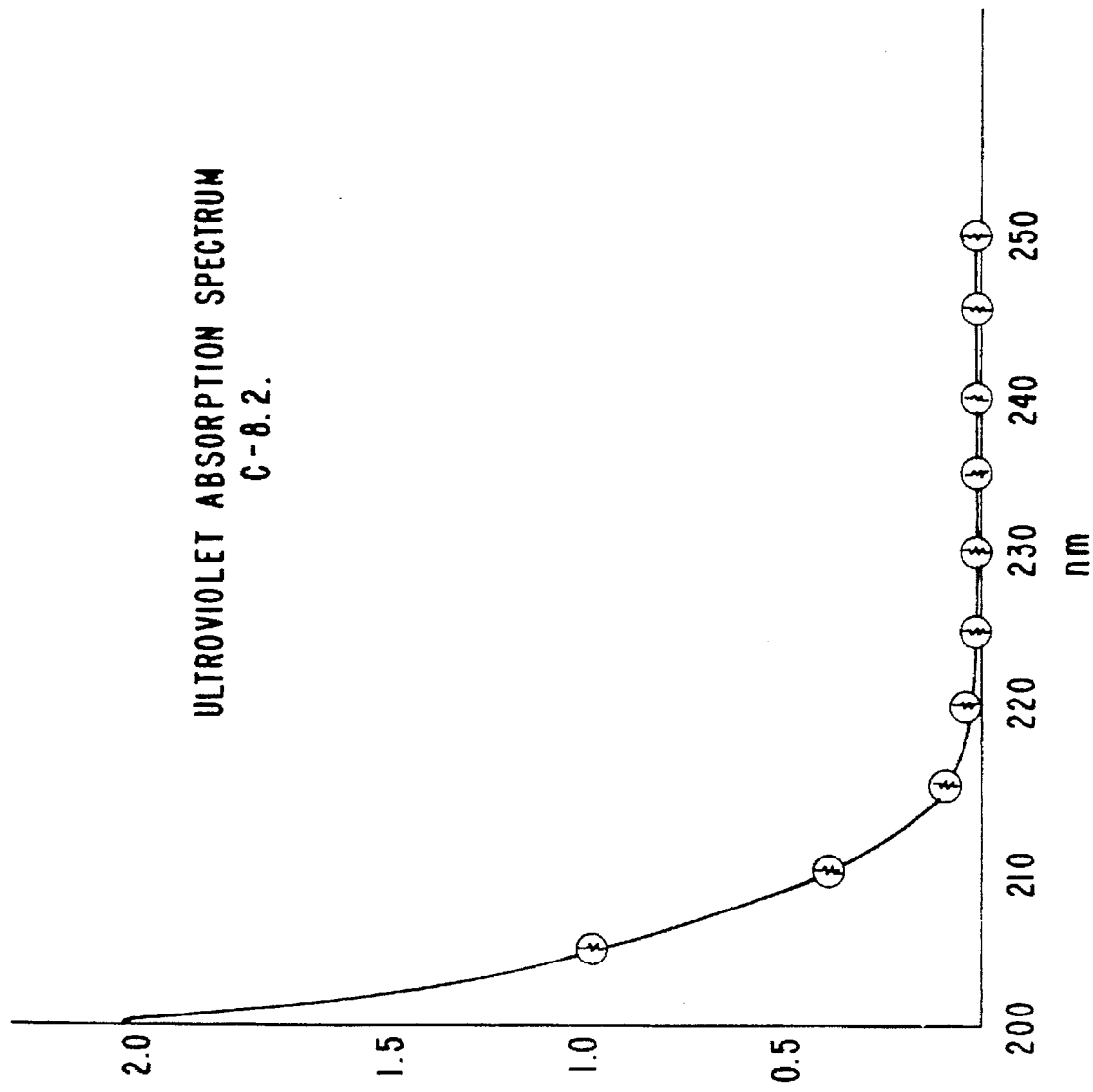
FIG. 6 is an ultraviolet (UV) spectrographic analysis of C-8.2

The UV absorption spectrum of C-8.2 is shown in FIG. 6. The significant portions of the spectrum are maximum absorption of 210 nm and shorter wavelengths and the absence of peaks in the range of 220 to 280 nm. The absence of the peaks at these wavelengths confirms the absence of aromatic groups such as amino acids, nucleic acids or pteridines.

FTIR Analysis

The Fourier Transform Infrared (FTIR) analysis spectrum of C-8.2 is shown in FIG. 7 (a and b). The spectra were obtained by a commercial laboratory (Hauser Chemicals, Golden Colorado).

The sample was dissolved in methanol and introduced to the FTIR spectrometer as a KBr pellet. A second spectrum was acquired using the microscope attachment. The spectra obtained were compared to reference spectra from known libraries for possible identification.

Figure 7A:
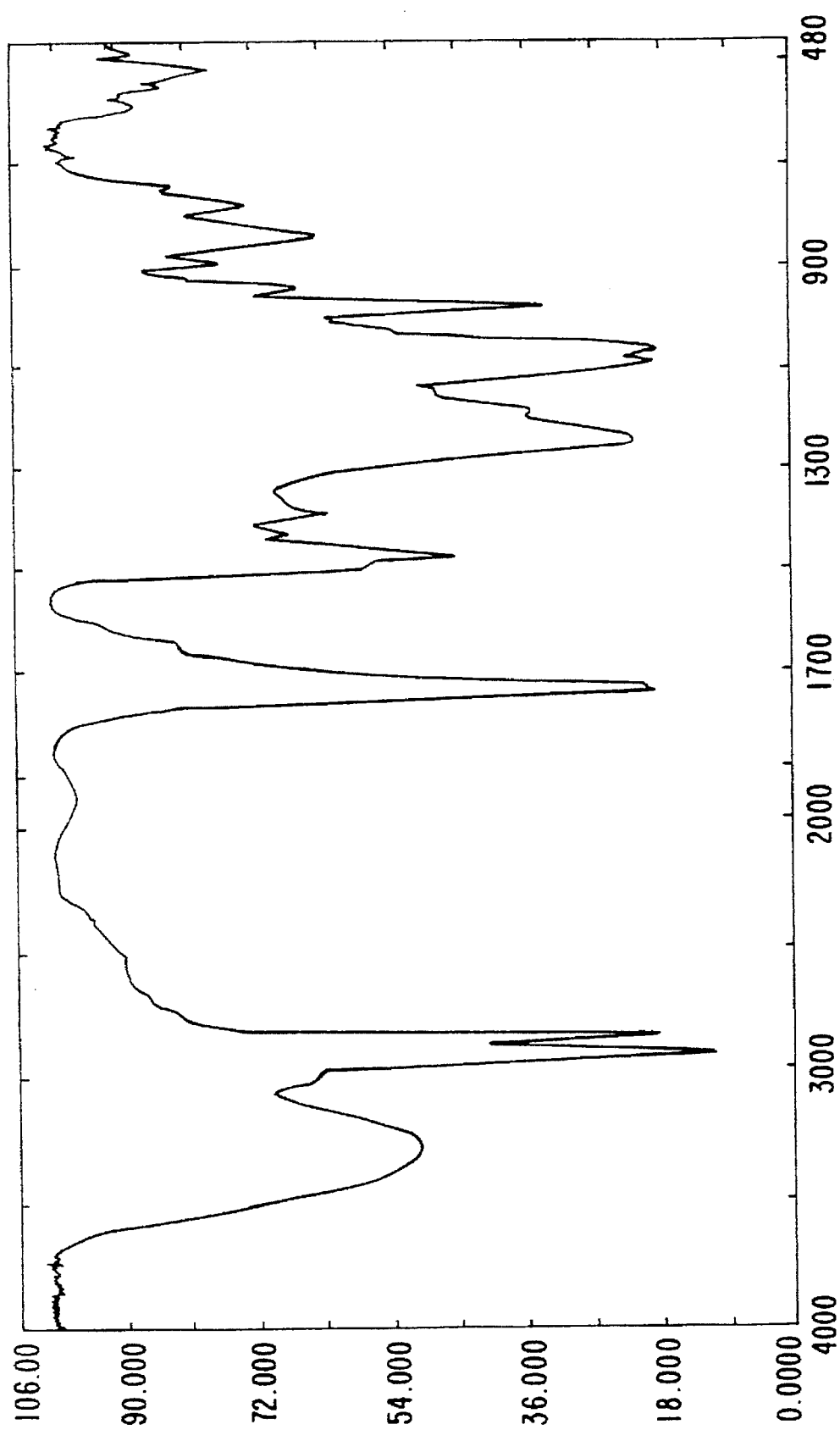
FIG. 7 (*a* and *b*) are Fourier Transform Infrared (FTIR) analyses of fraction number 25 isolated from an amino carbohydrate column in accordance with the methods of the present invention.
Figure 7B:
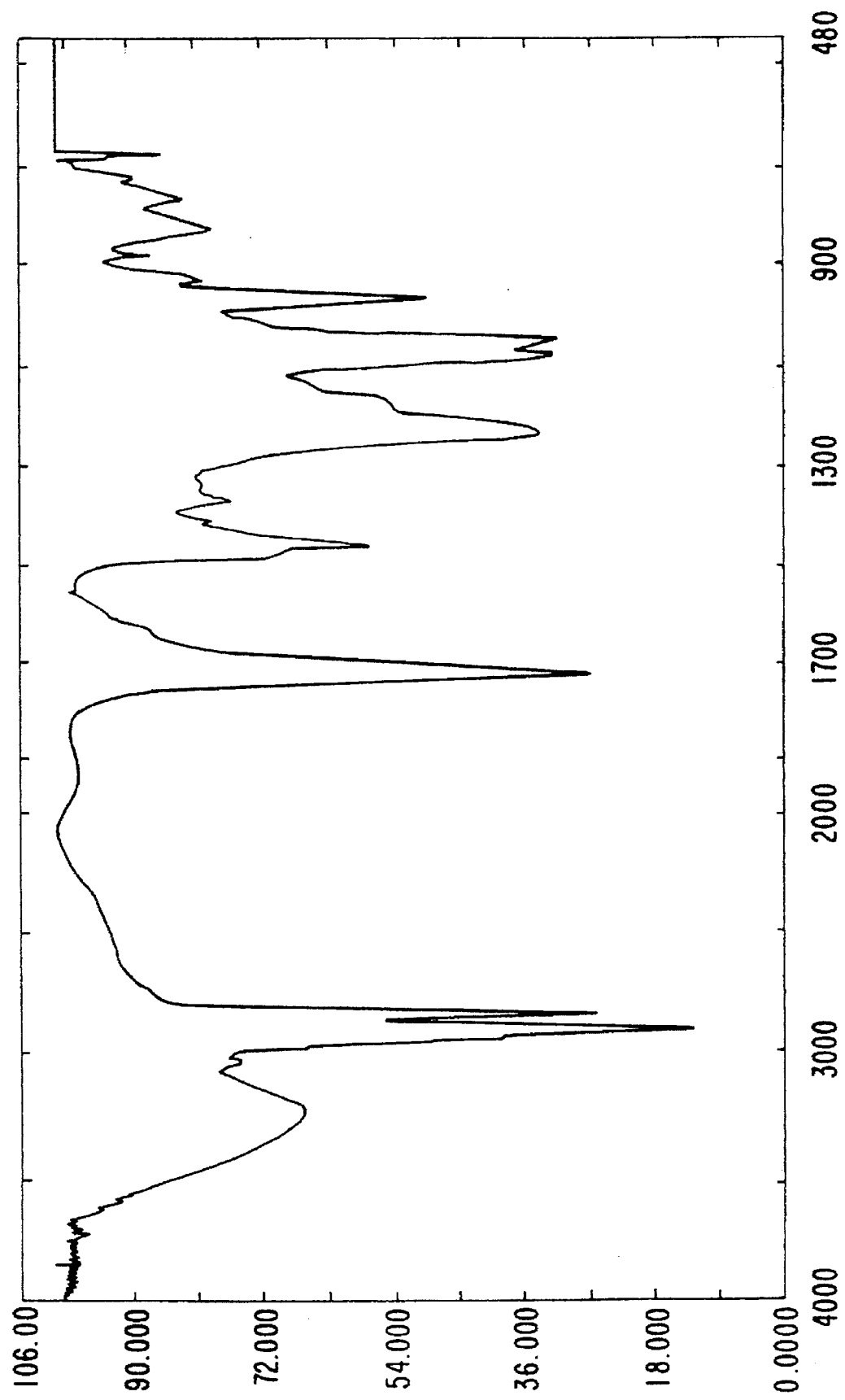

FIG. 7a represents the spectrum acquired on the sample prepared as a KBr pellet. FIG. 7b represents the FTIR spectrum acquired on the same sample using the microscope. FIGS. 8a and 8b are substantially identical. FIG. 8 represents a series of library spectra which comprise the five best fits from the available spectra data base.

The FTIR spectrum strongly suggested the presence of a carbonyl from an ester. The carbonyl was judged not to be conjugated. Additionally, the strong absorbance at 1249 $cm^{-1}$ is a positive indication of the presence of a P-O functional group. The broad absorbance at 3278 $cm^{-1}$ may be attributed to a hydroxyl functional group.

FAB-MS Analysis

Figure 11:
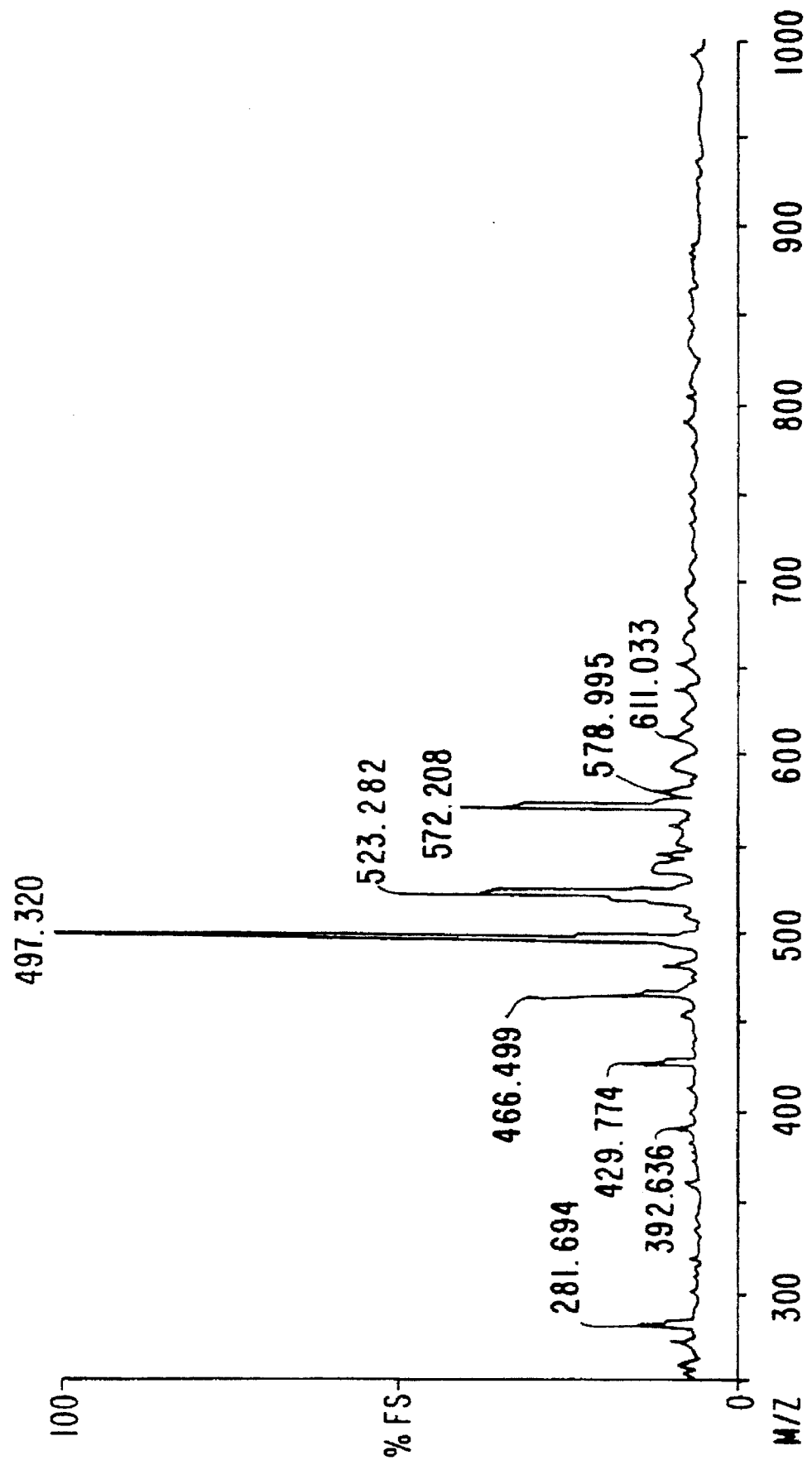
FIG. 11 is an FAB-MS analysis of fraction 25 obtained from an amino carbohydrate column of a sample from a normal individual in accordance with the methods of the present invention.

The mass spectrogram of C-8.2 is shown in FIGS. 9 and 11.

Figure 10:
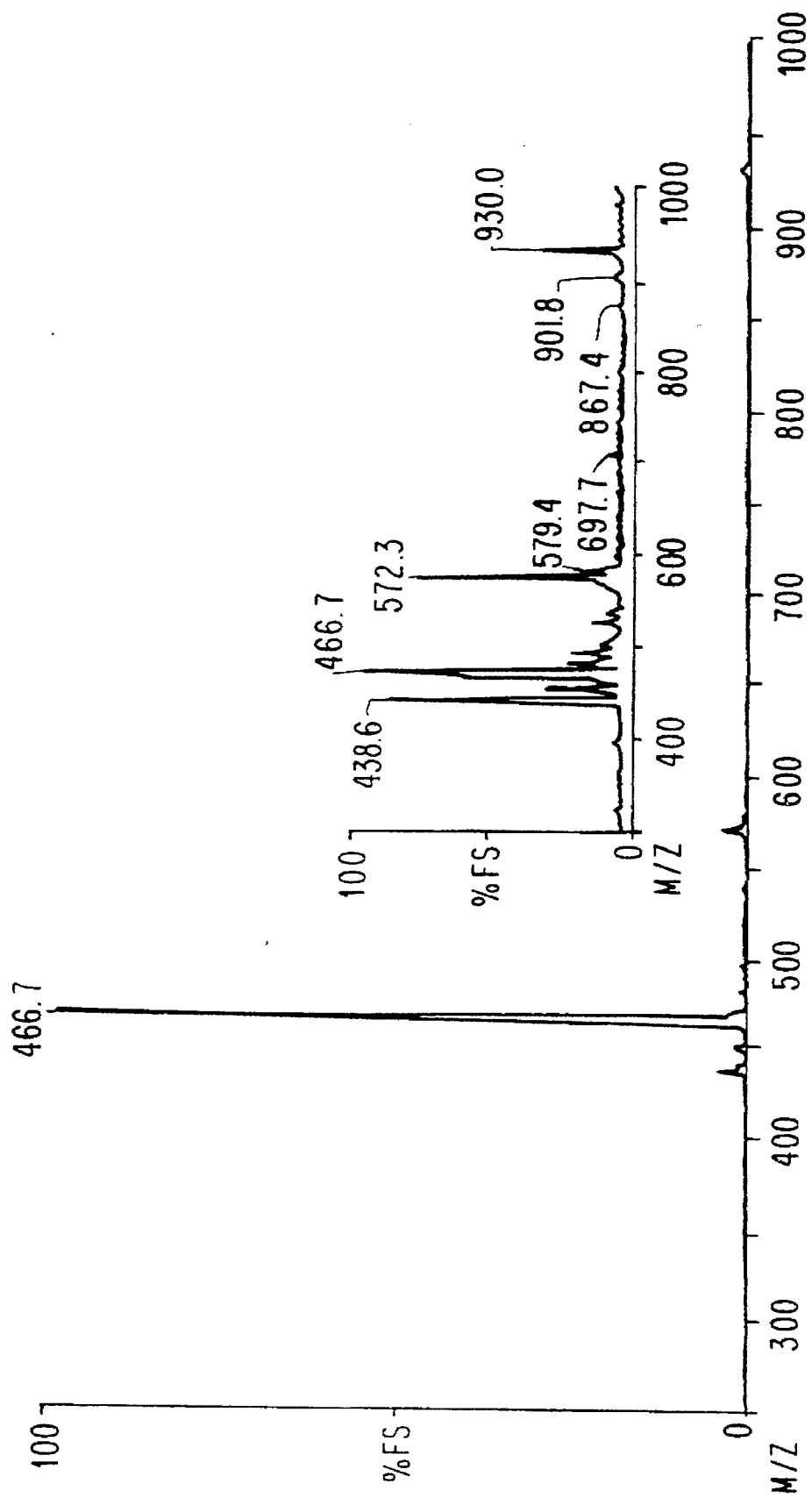
FIG. 10 is an FAB-MS analysis of sphingosylphosphoryl choline.

FIG. 9 depicts the FAB-MS spectrum of Fraction 24 mentioned above. In FIG. 9, the peak at 572 is from Gramicidin, added as an internal control. FIG. 10 depicts the FAB-MS spectrum of an authentic standard for spingosylphosphoryl choline (SPC The inset in FIG. 10 is an enlargement of the area of the control peaks. Comparing FIGS. 9 and 10, it can be seen that Fraction 24 contains SPC (having a peak at 466.7).

FIG. 11 depicts the FAB-MS spectrum of Fraction 25 as is lated from adult human serum. In FIG. 11, peaks at 523 and 572 were generated from internal standards added to Fraction 25 before analysis. The spectrum of Fraction 25 also has a peak at about 466, indicating that one component of C-8.2 is SPC.

Figure 12:
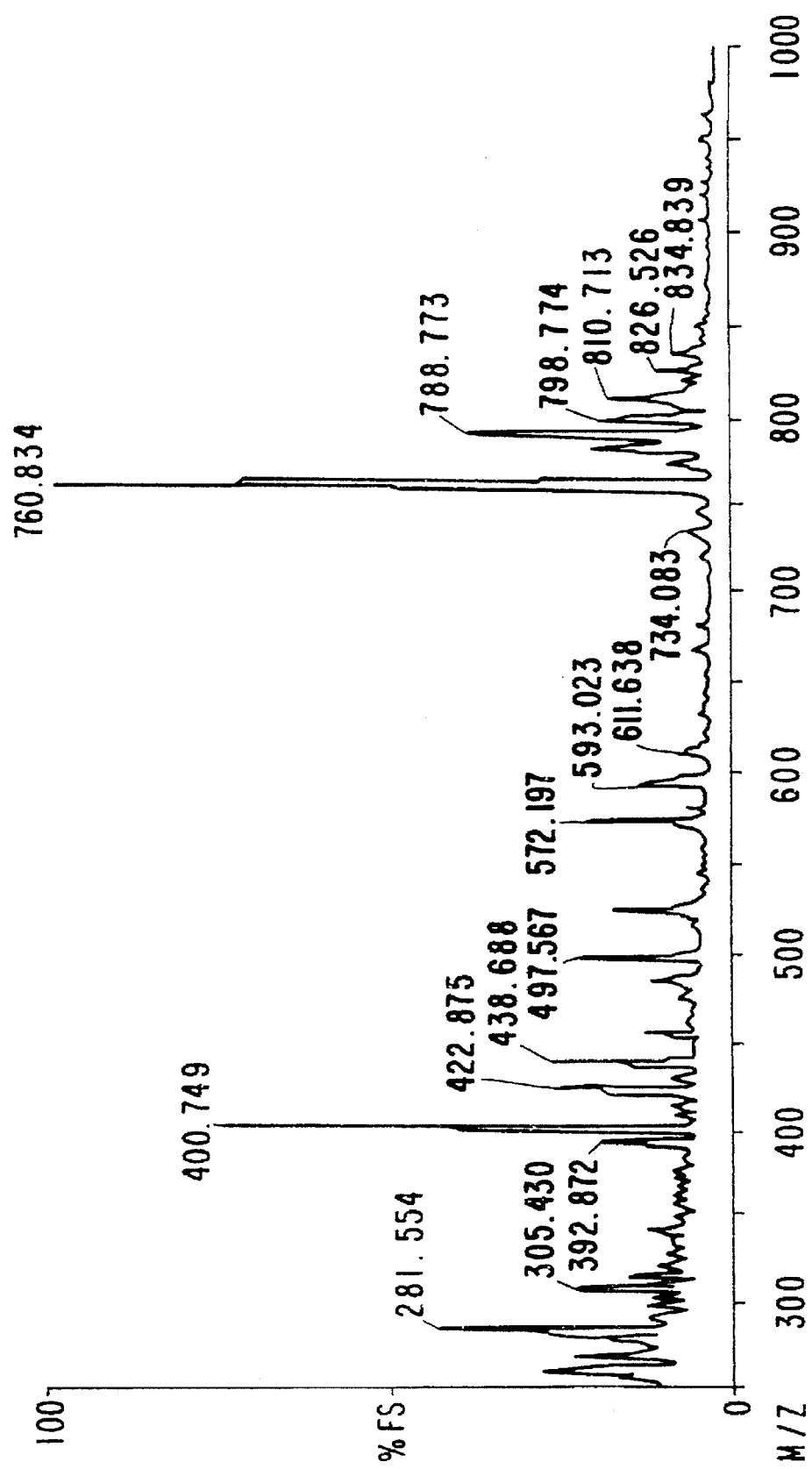
FIG. 12 is an FAB-MS analysis of phosphatidyl choline (lecithin).

FIG. 12 shows the spectrum for phosphatidyl choline (lecithin). The absence a peak at 760 in FIG. 11 (Fraction 25) and the absence of a peak at 497 (observed in FIG. 11) confirms that lecithin is not a component of C-8.2.

From the above FAB-MS analysis, it was concluded that SPC is a component of C-8.2.

Additional Purification Procedure

In order to get enough material to identify the structure of C-8.2, the isolation method was scaled up to 10 liters of serum.

The initial extraction method (mixing with 4 volumes of acetonitrile) was a duplicate of the method used above. The extract was then partitioned by the addition of benzene. The upper, organic, phase was evaporated to dryness and chromatographed on SEPHADEX198 LH-20 (Pharmacia, Piscataway, N.J.) with methanol as the solvent. All of the fractions containing material that eluted at 8.2 mins. (Nos. 8–12) were combined and concentrated by evaporation under vacuum. The pooled fractions were subjected to preparative HPLC (2 ml total in 0.35 ml batches). Each fraction was tested by analysis of an aliquot with the analytical HPLC column method described above. Material was found in the following fractions: (a) 24, (b) 25, (c) in lower concentrations in 26–31 designated as P2, and (d) in fractions 50 to 60 designated as P1. Mixing fractions did not indicate the presence of any doublets on the analytical column.

An aliquot (5% of the total) of fraction 25 was analyzed by FTIR. The pattern obtained was consistent with a phospholipid, sphingophosphoryl-choline but the complete structure of the lipid and its fatty esters could not be identified.

EXAMPLE 4

Identity of Surrogate Marker For HIV Infection

With the HPLC assay procedure described above, a large amount (100 mg) of C-8.2 was purified to apparent homogeneity from bovine blood (5 liters). The molecular weight of the product was determined to be a mixture of 758 and 786 daltons. This could be generated by the addition of linolenic acid as the acyl amide of sphingosyl-phospho-choline and the corresponding compound with 2 additional carbons. These structures have the trivial name of sphingomyelin. Sphingomyelin is not limited to linolenic-sphingosyl-phospho-choline, but also other fatty acid amides of sphingosy-phospho-choline. Authentic palmitoyl-sphingosyl-phospho-choline was obtained from Sigma Chemical Co. (St. Louis, Mo.) and used as a model compound. This authentic material had the same HPLC retention time as the isolated material (data not shown). FTIR was also consistent (data not shown). When analyzed by proton NMR, the model compound and the isolated material (i.e. C-8.2) had closely related spectra (data not shown).

Sphingomyelin is a major phospholipid component of cell membranes. The structural elements are: N-acyl-sphingosyl-phosphocholine, where the acyl group is usually either a 16 or 24 carbon fatty acid. In spite of high serum levels (in excess of 400 μmol/L or 35 mg/dl), the enzymes and regulatory mechanisms for both its synthesis and degradation are poorly characterized. Sphingomyelin is required for differentiation of macrophage/monocyte cells in response to phorbol esters. This process is protein kinase C dependent and inhibited by sphingosine. Thus, sphingomyelin and its precursors have an intimate role in differentiation of monocytes and may have a similar role in lymphocytes, including CD4+ cells.

Sphingomyelin is degraded to ceramides by the action of sphingomyelinase, which is an extracellular plasma membrane enzyme and is present in high concentrations in brain, liver and adrenals. Niemann-Pick syndrome is caused by an inherited defect in any one of five enzymes catalyzing degradation of sphingomyelin to ceramides, thus leading to high levels of sphingomyelin in serum. Individuals with this syndrome have an increased risk of developing autoimmune disorders, which may be caused by increased lymphocyte proliferation secondary to increased sphingomyelin levels.

Serum sphingomyelin levels are subject to tight metabolic control as illustrated by (a) the observed tight range in observed concentrations (35±3.5 mg/dL), (b) the lack of day to day variation and (c) the lack of change in concentration after a meal. However, the biochemical basis for this regulation is entirely unknown.

As described here, the observed natural course of sphingomyelin levels subsequent to HIV infection is (a) an immediate transient decrease, (b) a sustained increase when HIV-specific antibodies develop and (c) a return towards normal levels when AZT therapy is effective. The aforementioned increase is a consequence of the return of physiological control in the absence of HIV, in turn secondary to the antibody production. Serum sphingomyelin levels then increase until supranormal levels are attained. In response to AZT, sphingomyelin levels return towards normal levels from either extreme. These changes point to HIV as modulating the specific control pathway for serum sphingomyelin levels. If this were the case one could predict that there would be changes in lymphocyte differentiation secondary to these changes and this prediction is confirmed.

Without wishing to be bound by theory, it is believed that materials that interfere specifically with regulation of sphingomyelin synthesis or degradation may prevent retrovirus-directed subrogation of immune system cellular function. The initial decrease in serum sphingomyelin level may be caused by (a) increased degradation or (b) decreased synthesis. The initial target for therapy would be determined by the actual mechanism.

One of the first biochemical actions of HIV during infection is known to be decreased differentiation of CD4+ lymphocytes while later in the course of infection there is increased differentiation of CD8+ lymphocytes. Both of these effects may be mediated by changes in sphingomyelin concentration that are first reported in this application. Hence, enzymes controlling sphingomyelin levels present a new target to treat HIV infected individuals. Materials that bind to one of the enzymes and prevent the action of HIV on that enzyme would be of particular interest because they may prevent cell to cell transmission and thus permit non-antibody based immune function to eliminate infected cells. This type of process would lead to actual elimination of the infection rather than just its suppression.

What is claimed is:

1. A method for identifying a patient infected with HIV-1 comprising the steps of:
   detecting the amount of an agent selected from the group consisting of sphingomyelin, sphingosyl-phospho-choline and ceramides in a serum sample from said patient;
   wherein said patient is HIV-1 infected if the amount of said agent in said patient's serum sample is statistically different from the amount of said agent in serum samples obtained from a control, non-HIV-1 infected group.

2. A method as defined in claim 1, wherein said statistical difference is about three standard deviations.

3. A method as defined in claim 1, wherein said agent detecting step is performed by antibody-based assay.

4. A method as defined in claim 3, wherein said antibody-based assay is selected from the group consisting of IRMA, EIA, RIA and ELISA.

5. A method as defined in claim 1, wherein said detecting step is performed within about one week of infection with HIV-1 in said patient.

6. A method as defined in claim 5, wherein said detecting step is performed within about two days of infection with HIV-1 of said patient.

7. A method for identifying a patient infected with HIV-1 comprising the steps of:

a. obtaining a serum sample from said patient;

b. detecting the amount of an agent selected from the group consisting of sphingomyelin, sphingosyl-phospho-choline and ceramides in said sample; and c. comparing the amount of said agent in said sample with the amount of said agent present in a serum sample obtained from an age-matched control group of non-HIV-1 infected individuals;

wherein said patient is HIV-1 infected if the amount of said agent in said patient's sample is statistically different from the amount of said agent in said control group.

8. A method for determining the efficacy of the treatment of a human patient infected with HIV-1 comprising the steps of:

a. detecting the amount of an agent selected from the group consisting of sphingomyelin, sphingosyl-phospho-choline and ceramides in a serum sample from said patient before said treatment; and b.
  i. detecting the amount of said agent in a serum sample from said patient during said treatment; or
  ii. detecting the amount of said agent in a serum sample from said patient after said treatment;

wherein said treatment is effective if the amount of said agent in said sample of step a. is statistically different from the amount of said agent in said sample of step b.

9. A method as defined in claim 8, wherein said statistical difference is about three standard deviations.

10. A method as defined in claim 8, wherein said agent quantifying steps a., b., or a. and b. are performed by antibody-based assay.

11. A method as defined in claim 10, wherein said antibody-based assay is selected from the group consisting of IRMA, EIA, RIA and ELISA.

12. A method as defined in claim 8 wherein said treatment comprises the administration of a member selected from the group consisting of AZT, ddI, ddC or mixtures thereof to said patient.

13. A method for determining the efficacy of the treatment of a human patient infected with HIV-1 comprising the steps of:

a. obtaining a serum sample from said patient before said treatment;

b. detecting the amount an agent selected from the group consisting of sphingomyelin, sphingosyl-phospho-choline and ceramides in said sample of step a.;

c.
  i. obtaining a serum sample from said patient during said treatment; or
  ii. obtaining a serum sample from said patient after said treatment; and d. detecting the amount of said agent in said sample of step c.;

e. comparing the amount of said agent in said sample of step a. with the amount of said agent in said sample of step c;

wherein said treatment is effective if the amount of said agent in said sample of step a. is statistically different from the amount of said agent in said sample of step c.

14. A method for identifying a patient infected with HIV-1 comprising the steps of:

obtaining a serum sample from said patient, detecting the amount of an agent selected from the group consisting of sphingomyelin, sphingosyl-phospho-choline and ceramides in said serum sample, comparing the amount of said agent in said serum sample with that of the amount of said agent present in a serum sample obtained from age-matched control, non-HIV-1 infected group, wherein said patient is HIV-1 infected if the amount of said agent in said patient's serum sample is statistically different from the amount of said agent in said control, non-HIV infected group.

15. The method of claim 14 wherein said statistical difference is about three standard deviations.

16. The method of claim 14 wherein said agent quantifying step is performed by antibody-based assay.

17. The method of claim 14 wherein said agent is quantified using an antibody-based test selected from this group consisting of IRMA, EIA, RIA and ELISA.

* * * * *